United States Patent
Mescher et al.

(10) Patent No.: US 10,376,884 B2
(45) Date of Patent: Aug. 13, 2019

(54) ACTUATED VALVE OR PUMP FOR MICROFLUIDIC DEVICES

(71) Applicant: The Charles Stark Draper Laboratory, Inc., Cambridge, MA (US)

(72) Inventors: Mark Joseph Mescher, West Newton, MA (US); Jonathan Robert Coppeta, Windham, NH (US); Abigail June Spencer, Boston, MA (US); Brett Isenberg, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 481 days.

(21) Appl. No.: 15/016,227

(22) Filed: Feb. 4, 2016

(65) Prior Publication Data
US 2016/0220997 A1   Aug. 4, 2016

Related U.S. Application Data
(60) Provisional application No. 62/111,978, filed on Feb. 4, 2015.

(51) Int. Cl.
  *B01L 3/00*  (2006.01)
  *C12M 3/00*  (2006.01)
  (Continued)

(52) U.S. Cl.
  CPC ....... *B01L 3/502738* (2013.01); *C12M 21/08* (2013.01); *C12M 23/16* (2013.01);
  (Continued)

(58) Field of Classification Search
  CPC ...... C12M 21/08; C12M 23/16; C12M 29/12; C12M 27/00; A61M 2205/0244;
  (Continued)

(56) References Cited

U.S. PATENT DOCUMENTS

| 5,142,781 A | 9/1992 | Mettner et al. |
| 7,438,030 B1 | 10/2008 | Okojie |

(Continued)

FOREIGN PATENT DOCUMENTS

| EP | 0 823 483 A1 | 2/1998 |
| EP | 1 932 904 | 6/2008 |

(Continued)

OTHER PUBLICATIONS

Grover, William, et al., "Monolithic membrane valves and diaphragm pumps for practical large-scale integration into glass microfluidic devices", Sensors and Actuators B 89 (2003) pp. 315-323.

(Continued)

*Primary Examiner* — Lyle Alexander
*Assistant Examiner* — Bryan Kilpatrick
(74) *Attorney, Agent, or Firm* — McDermott Will & Emery LLP

(57) ABSTRACT

Systems and methods disclosed herein related to an apparatus including a fluid flow plate and a microfluidic valve assembly. The fluid flow plate includes a plurality of polymer layers that define a fluid flow passage through the microfluidic valve assembly. The microfluidic valve assembly includes a valve seat, a flexible membrane, a valve cavity, a valve head, and an actuator. The actuator is configured to selectively control pressure applied by the valve head to the flexible membrane, such that in a first actuator state the valve head depresses the flexible membrane into the valve cavity and into contact with the valve seat, thereby preventing fluid flow through the valve assembly, and in a second state, the valve head and the flexible membrane are retracted substantially out of the valve cavity allowing fluid to flow through the valve assembly. In various implementations, the valve seat and/or the flexible membrane include an elastomer layer.

21 Claims, 19 Drawing Sheets

(51) Int. Cl.
*C12M 3/06* (2006.01)
*F16K 99/00* (2006.01)
*F16K 7/12* (2006.01)

(52) U.S. Cl.
CPC .......... *F16K 7/126* (2013.01); *F16K 99/0015* (2013.01); *B01L 2200/027* (2013.01); *B01L 2300/0816* (2013.01); *B01L 2300/12* (2013.01); *B01L 2300/123* (2013.01); *B01L 2300/14* (2013.01); *B01L 2400/0638* (2013.01); *B01L 2400/082* (2013.01); *F16K 2099/008* (2013.01)

(58) Field of Classification Search
CPC ................ A61M 39/22; A61M 5/1452; A61M 5/14526; F16K 2099/008; F16K 99/0015; F16K 99/0001; F16K 99/0055; B01L 2200/027; B01L 2300/123; B01L 2300/14; B01L 2400/0638; G05D 7/012; G05D 7/0694; Y10T 137/0396; F04B 43/043

See application file for complete search history.

(56) References Cited

U.S. PATENT DOCUMENTS

| | | |
|---|---|---|
| 7,445,926 B2 | 11/2008 | Mathies et al. |
| 8,318,479 B2 | 11/2012 | Domansky et al. |
| 2002/0124897 A1 | 9/2002 | Bergh et al. |
| 2005/0001182 A1 | 1/2005 | Wise et al. |
| 2005/0238506 A1* | 10/2005 | Mescher ........... A61M 5/14276 417/413.1 |
| 2005/0260745 A1 | 11/2005 | Domansky et al. |
| 2006/0199260 A1 | 9/2006 | Zhang et al. |
| 2006/0281143 A1 | 12/2006 | Liu et al. |
| 2008/0249510 A1* | 10/2008 | Mescher ........... A61M 5/14276 604/890.1 |
| 2009/0305397 A1 | 12/2009 | Dodgson et al. |
| 2010/0303687 A1 | 12/2010 | Blaga et al. |
| 2011/0039303 A1 | 2/2011 | Jovanovich et al. |
| 2012/0214189 A1 | 8/2012 | Shuler et al. |
| 2014/0212964 A1 | 7/2014 | Cuiffi et al. |

FOREIGN PATENT DOCUMENTS

| | | |
|---|---|---|
| WO | WO-97/04074 | 2/1997 |
| WO | WO-2007/021343 | 2/2007 |
| WO | WO-2011/014674 | 2/2011 |

OTHER PUBLICATIONS

Gu, Wei, et al., "Computerized microfluidic cell culture using elastomeric channels and Braille displays", PNAS, Nov. 9, 2004, vol. 101, No. 45, pp. 15861-15866.
International Preliminary Report on Patentability dated Feb. 5, 2015 in PCT Application No. PCT/US2013/052089.
International Preliminary Report on Patentability dated Aug. 13, 2015 in PCT Application No. PCT/US2014/013604.
International Search Report and Written Opinion for PCT/US2013/052089 dated Oct. 31, 2013.
International Search Report and Written Opinion dated May 20, 2014 in PCT Application No. PCT/US2014/013604.
U.S. Notice of Allowance in U.S. Appl. No. 14/167,590 dated Sep. 22, 2015.
U.S. Office Action in U.S. Appl. No. 14/167,590 dated Jun. 11, 2015.
U.S. Office Action in U.S. Appl. No. 13/951,067 dated Mar. 20, 2015.
U.S. Office Action in U.S. Appl. No. 13/951,067 dated Jul. 8, 2015.
U.S. Office Action on U.S. Appl. No. 13/951,067 dated Mar. 31, 2016.
Zhang, Chi, et al., "Towards a human-on-chip: Culturing multiple cell types on a chip with compartmentalized microenvironments", Lab on a Chip, vol. 9, No. 22, Nov. 21, 2009, pp. 3165-3312.
International Search Report and Written Opinion dated Jun. 9, 2016 in PCT Application No. PCT/US2016/016666, 11 pages.

* cited by examiner

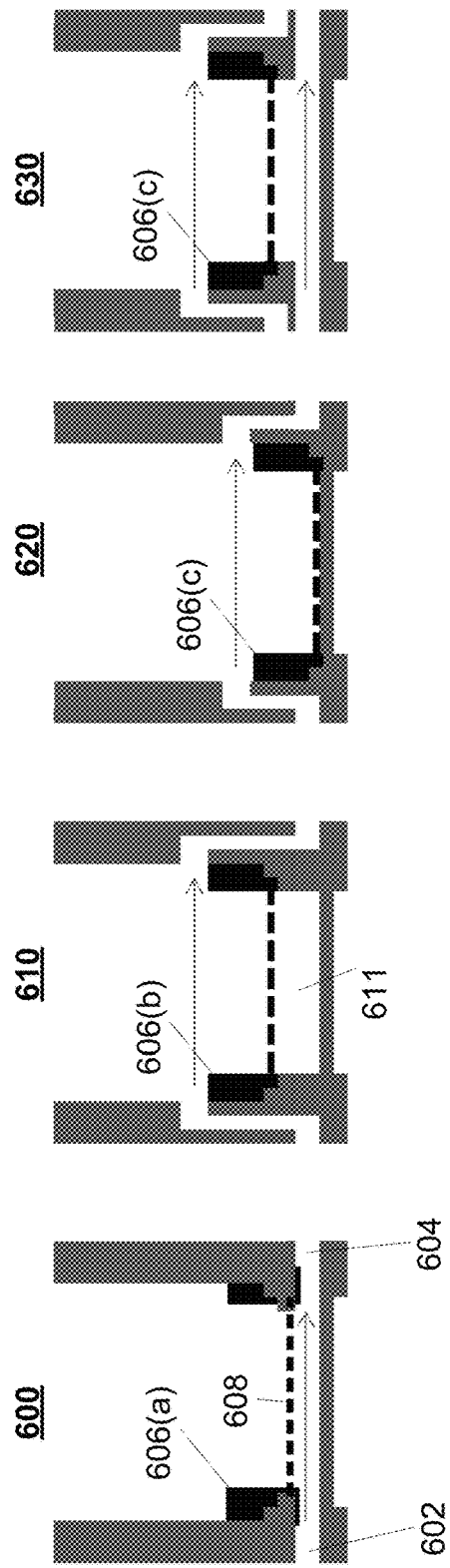

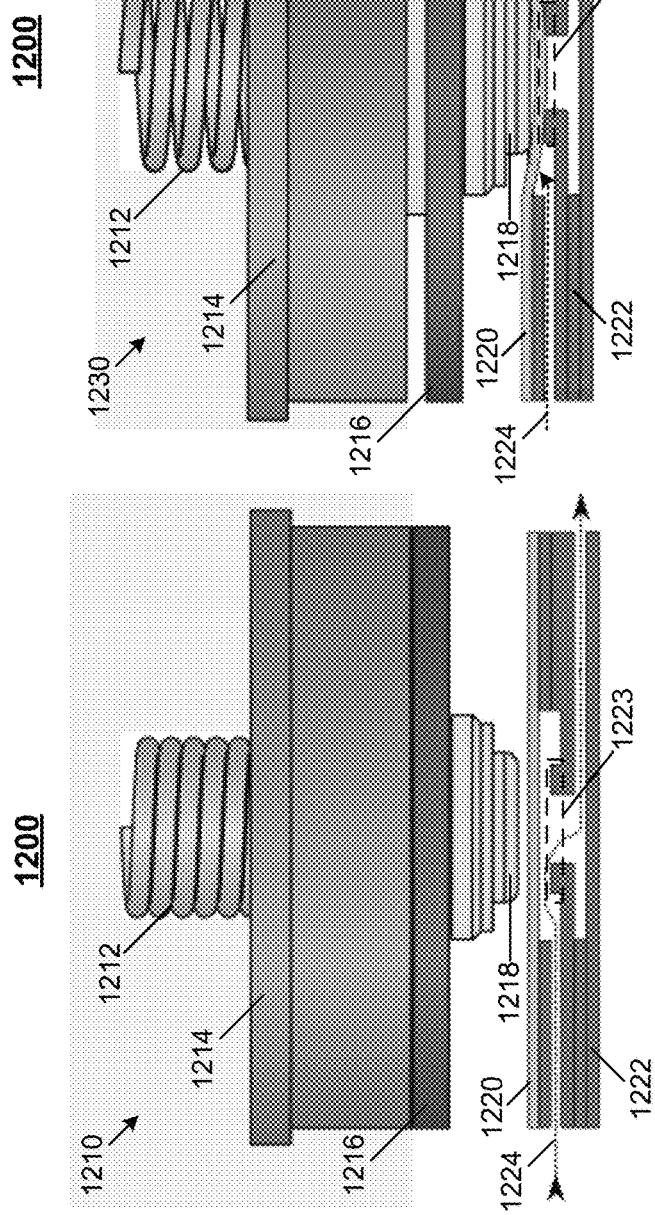

ACTUATED VALVE OR PUMP FOR MICROFLUIDIC DEVICES

CROSS-REFERENCE TO RELATED PATENT APPLICATIONS

This application claims priority to Provisional U.S. Patent Application 62/111,978, filed Feb. 4, 2015, which is incorporated herein by reference in its entirety.

BACKGROUND OF THE DISCLOSURE

In vitro models of human tissue are typically cultured as single cultures in isolated environments. The isolation of the tissue cultures removes the interplay between the tissue cultures that is present in in vivo systems. The isolated tissue environments make it difficult to study systemic issues, such as drug dosing, in in vitro cultures.

SUMMARY OF THE DISCLOSURE

According to one implementation of the disclosure, an apparatus includes a fluid flow plate with a plurality of polymer layers. The fluid flow plate defines a fluid flow passage through a microfluidic valve assembly. The valve assembly includes a valve seat, a flexible membrane including an elastomer layer, a valve cavity positioned between the valve seat and the. flexible membrane, and a valve head. The valve assembly also includes an actuator configured to selectively control pressure applied by the valve head to the flexible membrane. In a first actuator state the valve head depresses the flexible membrane into the valve cavity and into contact with the valve seat, thereby preventing fluid flow through the valve assembly. In a second state, the valve head and the flexible membrane are retracted substantially out of the valve cavity allowing fluid to flow through the valve assembly.

In some implementations, the flexible membrane is corrugated. In some implementations, the valve seat is annular in shape, and the corrugations of the membrane are formed as concentric annular shapes that are coaxial to and outside the annulus of the valve seat.

In some implementations, the fluid flow plate includes a flexible load distribution layer coupled to a valve seat facing side of the flexible membrane. The load distribution layer can have a cutout above the valve seat. The diameter of the cutout in the load distribution layer is larger than an outer diameter of the valve seat and less than a diameter of the valve cavity.

In some implementations, the apparatus includes an anti-stiction coating disposed on at least one of a valve head facing surface of the flexible membrane over an area corresponding to a valve head footprint, a valve seat facing surface of the flexible membrane over an area corresponding to a valve seat footprint, and a membrane facing surface of the valve seat. In some implementations, the apparatus includes a vacuum chamber that is defined by an airtight housing and a valve head facing surface of the flexible membrane.

In some implementations, the flexible membrane has a tensile strain in the second state of between about 0.25% and about 2.0%. In some implementations, the valve seat has a resting tensile strain in the second state of between about 0.25% and about 2.0%. In some implementations, the flexible membrane includes a biocompatible metal.

In some implementations, the elastomer layer includes a plurality of lateral strain relief cutouts disposed radially about an area corresponding to a valve seat footprint of the elastomer layer. In some implementations, the valve seat includes an elastomer layer.

According to another implementation, the apparatus includes a pump assembly. The pump assembly can include a flexible membrane including an elastomer layer, an actuator, a pump head on a first side of the flexible membrane, and a pump cavity on an opposite side of the flexible membrane relative to the pump head. In a first actuator state the pump head of the pump assembly depresses the flexible membrane into the pump cavity and drives a fluid from the pump cavity. In a second state, the pump head and the flexible membrane are retracted substantially out of the pump cavity to draw fluid into the pump cavity.

According to another aspect of the disclosure, an apparatus includes a fluid flow plate includes a plurality of polymer layers. The fluid flow plate defines a fluid flow passage through a microfluidic valve assembly. The valve assembly includes a valve seat comprising an elastomer layer, a flexible membrane, a valve cavity positioned between the valve seat and the flexible membrane, and a valve head. The valve assembly also includes an actuator configured to selectively control pressure applied by the valve head to the flexible membrane. In a first actuator state the valve head depresses the flexible membrane into the valve cavity and into contact with the valve seat, thereby preventing fluid flow through the valve assembly. In a second state, the valve head and the flexible membrane are retracted substantially out of the valve cavity allowing fluid to flow through the valve assembly.

In some implementations, the flexible membrane is corrugated. In some implementations, the valve seat is annular in shape, and the corrugations of the membrane are formed as concentric annular shapes that are coaxial to and outside the annulus of the valve seat.

In some implementations, the fluid flow plate includes a flexible load distribution layer coupled to a valve seat facing side of the flexible membrane. The load distribution layer can have a cutout above the valve seat. The diameter of the cutout in the load distribution layer can be larger than an outer diameter of the valve seat and less than a diameter of the valve cavity.

In some implementations, an anti-stiction coating is disposed on at least one of a valve head facing surface of the flexible membrane over an area corresponding to a valve head footprint, a valve seat facing surface of the flexible membrane over an area corresponding to a valve seat footprint, and a membrane facing surface of the valve seat.

In some implementations, the apparatus includes a vacuum chamber defined by an airtight housing and a valve head facing surface of the flexible membrane. In some implementations, the flexible membrane has a tensile strain in the second state of between about 0.25% and about 2.0%. In some implementations, the valve seat has a resting tensile strain in the second state of between about 0.25% and about 2.0%. In some implementations, the flexible membrane is formed of at least one of an elastomer and a biocompatible metal. In some implementations, the membrane includes a second elastomer layer and the second elastomer layer includes a plurality of lateral strain relief cutouts disposed radially about an area corresponding to a valve seat footprint of the elastomer layer.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 6A-6D illustrate example configurations of cell culture vessels that can be used in the cell culture system of FIG. 1.

FIGS. 12A and 12B are cross-sectional illustrations of two configurations of a valve assembly, according to an example arrangement.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods disclosed are generally related to a cell culture system. More particularly, the systems and methods enable culturing and interconnecting a plurality of tissue types in a biomimetic environment. By culturing organ specific tissue types within a biomimetic environment and interconnecting each of the organ systems in a physiologically meaningful way, experiments can be conducted on in vitro cells that substantially mimic the responses of in vivo cell populations. In some implementations, the system is used to monitor how organ systems respond to agents such as toxins or medications. The system enables the precise and controlled delivery of these agents, which, in some implementations, allows the biomimetic dosing of drugs in humans to be mimicked.

Figure 1:
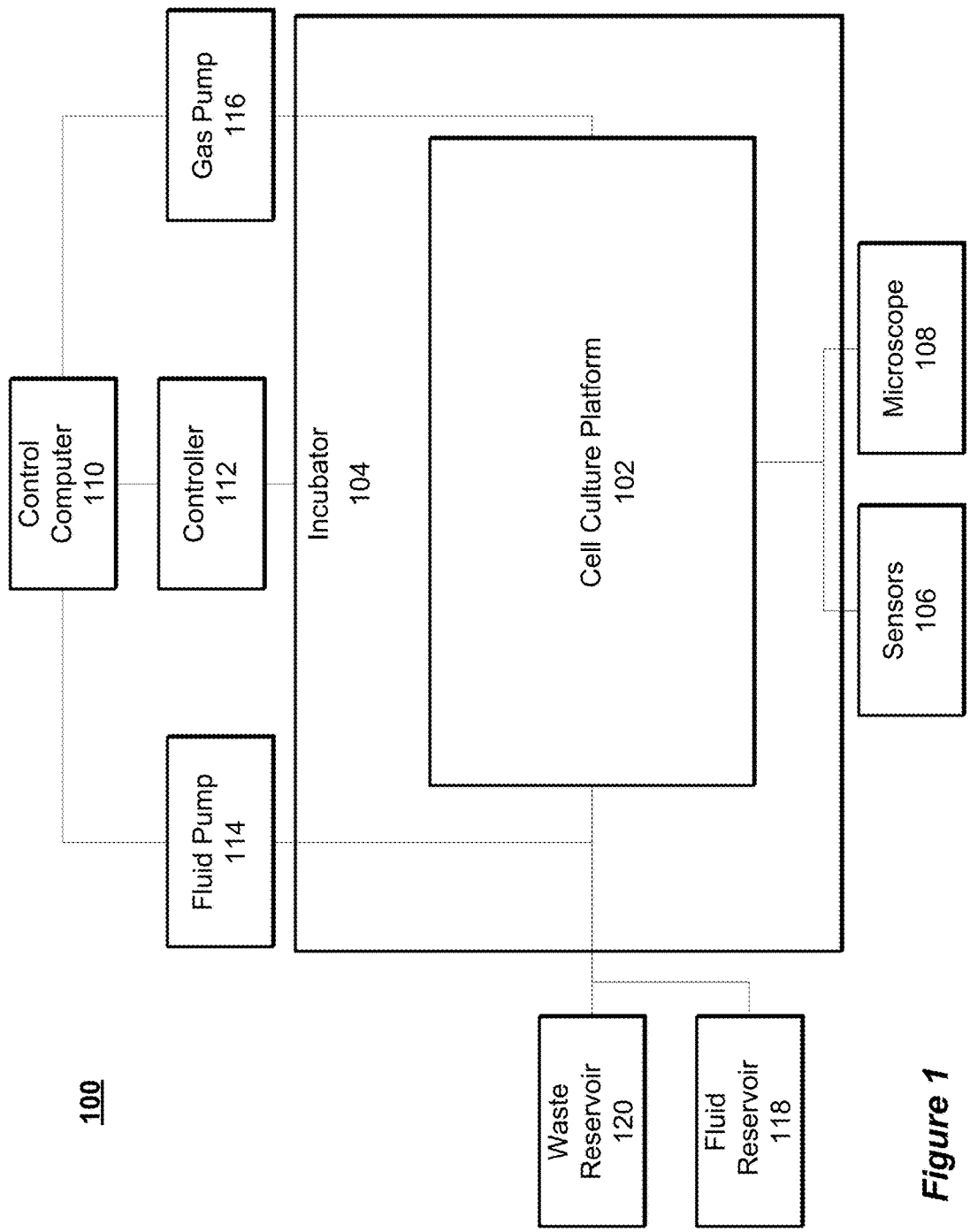
FIG. 1 is a schematic of a cell culture system.

FIG. 1 illustrates a cell culture system 100. The cell culture system 100 includes a cell culture platform 102 within an incubator 104. The cell culture system 100 also includes a plurality of sensors 106 and a microscope 108 to monitor the cells within the cell culture platform 102. A control computer 110 uses a controller 112 to control the flow of fluids and gases through the cell culture platform 102. The fluid flow and gas flow is caused by at least one fluid pump 114 and at least one gas pump 116, respectively. Prior to flowing through the cell culture platform 102, fluid is stored in a fluid reservoir 118 and responsive to flowing through the cell culture platform 102 the fluid is stored in a waste reservoir 120.

As described above, the cell culture system 100 includes a cell culture platform 102. The cell culture platform 102 and its components are described further in relation to FIGS. 2-9, but briefly, the cell culture platform 102 is a modular platform for culturing cells and/or tissue. As discussed below, the cell culture platform 102 includes a control plate, a fluid flow plate and a plurality of cell culture vessels. In some implementations, the control plate is reusable and includes actuators, valves and sensors used in the culture and monitoring of cells. In some implementations, the fluid flow plate and/or the cell culture vessels are disposable.

The cell culture platform 102 is housed within an incubator 104. The incubator 104 maintains an environment within the cell culture platform 102 that is conducive for the culturing of the cells and/or tissue. In some implementations, the incubator 104 controls and/or maintains a predetermined temperature, humidity, carbon dioxide level, oxygen level, or any combination thereof. For example, the incubator 104 may be configurable to maintain conditions within the cell culture platform 102 that mimic conditions within the human respiratory system. In another example, the incubator 104 is configured to maintain standard cell culture environments, as outlined by a cell culture protocol. For example, the incubator 104 can maintain a temperature between about 32° C. and about 37° C. with humidity between about 50% and about 100%. In some implementations, the incubator 104 removes off gases generated by the cells within the cell culture platform 102. The incubator 104 also includes a plurality of access ports (not illustrated). The ports allow sensor connections, flow lines, and other lines to pass from the outside environment to the interior of the incubator 104 without affecting the controlled environment within the incubator 104.

In some of these implementations, the cell culture system 100 does not include a standalone incubator 104. In those implementations, the cell culture vessels of the cell culture platform 102 are reversibly sealed and include heating and other elements that maintain an appropriate environmental condition within each cell culture vessel.

The cell culture system 100 also includes a plurality of sensors 106. In some implementations, one or more of the sensors 106 described herein are housed within (or a component of) the cell culture platform 102. A further description of the sensors 106, including their use and placement, is described below. In brief, the sensors 106 can be used to monitor one or more parameters within the cell culture platform 102. For example, the sensors 106 can monitor biomarkers, flow rates, pressures, temperatures, gas compositions (e.g., oxygen and carbon dioxide levels), chemical compositions (e.g., drug, toxin and metabolite concentrations), pH levels, electrical parameters (e.g., trans-epithelial electrical resistance) or any combination thereof. In some implementations, the sensors are used for feedback by the control computer 110 in controlling system parameters (e.g., environmental conditions) within the cell culture platform 102 and/or incubator 104.

Also as illustrated in FIG. 1, the cell culture system 100 includes a microscope 108. In some implementations, at least a portion of the cell culture platform 102 is configured to allow visual inspectional of the cells and/or tissue within the cell culture platform 102. For example, the components of the cell culture platform 102 are manufactured from substantially clear materials and/or include view ports. The microscope 108 is used to view cells and/or tissue cultured in the cell culture platform 102. In some implementations, the microscope 108 is configured to record still or moving images of the cells and/or tissue within the cell culture platform 102. In some implementations, the microscope 108 is an optical light microscope, confocal microscope, fluorescent microscope, or, in general, any type of microscope used in the field of cellular imaging and analysis.

The cell culture system 100 further includes a control computer 110 and a controller 112. In general, the control computer 110 controls the components described herein of the cell culture system 100. In some implementations, the control computer 110 is a general purpose computing device. For example, the control computer 110 can be a laptop, tablet computer, or smartphone. In other implementations, the control computer 110 is a special purposed computer device and includes one or more processors and at least one computer readable medium, such as a hard drive, compact discs, or other storage device. Processor executable instructions are stored on the computer readable medium. When executed, the instructions cause the control computer 110 to perform the functions and methods described herein. For example, the control computer 110 controls the flow of a fluid into and out of the cell culture platform 102 by controlling fluid pumps 114. As described above, in some implementations the control computer 110 receives data from the plurality of sensors 106 and maintains system conditions responsive to the received data. The control computer 110 stores the sensor and other data on the computer readable medium in response to a request from a user. In some implementations, the control computer 110 enables a user to set specific system parameters through a user interface.

The control computer 110 interfaces with the other components of the cell culture system 100 through a controller 112. In some implementations, the controller 112 is a component of the control computer 110 or the cell culture platform 102, and is implemented as hardware and/or software. In other implementations, the controller 112 is a standalone device that interfaces with the control computer 110 and various components of the cell culture system 100 through USB, Firewire, or a similar connection.

The controller includes a plurality of inputs and a plurality of outputs through which it interfaces with the various components of the cell culture system 100. The plurality of inputs and outputs of the controller 112 can be digital and/or analog inputs and outputs. In some implementations, the controller 112 includes at least one processor. Using the at least one processor, the controller 112 preprocesses inputs prior to transmitting the input to the control computer 112. For example, the controller 112 may "pre-filter" or compress sensor data before transmitting the sensor data to the control computer 110. In yet other implementations, instructions are loaded onto the controller 112 such that the controller 112 can control the cell culture system 100 without instruction from the control computer 110. In some implementations, the controller 112 and/or computer 110 alert a user when the cell culture system 100 behavior deviates from predetermined ranges. For example, the control computer 110 may send an alert to the user when the control computer 110 detects a temperature drop in the incubator 104.

Referring again to FIG. 1, the cell culture system 100 includes at least one fluid pump 114 and at least one gas pump 116. The fluid pump 114 and the gas pump 116 (collectively referred to simply as pumps) flow liquids and/or gases into and through the cell culture platform 102. Extra fluid is stored within the fluid reservoir 118 and can be deposited into a waste reservoir after flowing through the cell culture platform 102. In other implementations, the fluid is recirculated through the cell culture platform 102. As illustrated, the pumps are independent from the cell culture platform 102. As described below, in some implementations, the pumps are housed within the cell culture platform 102. The pumps can include peristaltic pumps, syringe pumps, a series of actuators (i.e., pneumatic pumps), or any combination thereof. In some implementations the pumps are configured to produce a smooth flow, pulsatile flow, periodic flow, or any combination thereof through the cell culture platform 102. In yet other implementations, the pumps are directional and can serve as one way valves within the cell culture platform 102. For example, one way pumps can be included within the cell culture platform 102 to force flow in a predetermined manner and not allow backflow during a pulsatile flow.

The foregoing pumps flow a fluid through the cell culture platform 102 and into the below described cell culture vessels. Example fluids include growth medium (or other fluids for cellular growth and sustenance), test agents, toxins, medicaments (e.g., antibiotics, vaccines, biologics, and medical countermeasures), or any combination thereof. In some implementations, the pumps are configured to induce a predetermined shear force on the cells within the cell culture platform 102. The shear force may be selected to mimic physiological conditions or for experimental purposes. For example, epithelial cells may form more physiologically representative cellular barriers when cultured under an appropriate shear force. In some implementations, the flow rates at which the pumps flow fluid are selected to mimic blood flow rates typically seen in parts of the circularity system. In some cases, the system may include a combination of cell types (prokaryotic and/or eukaryotic) to mimic a biological use case such as the microbiome lining the intestinal tract. In other cases viruses, bacteria, or phages are introduced to mimic a biological process such as a disease state.

Figure 2:
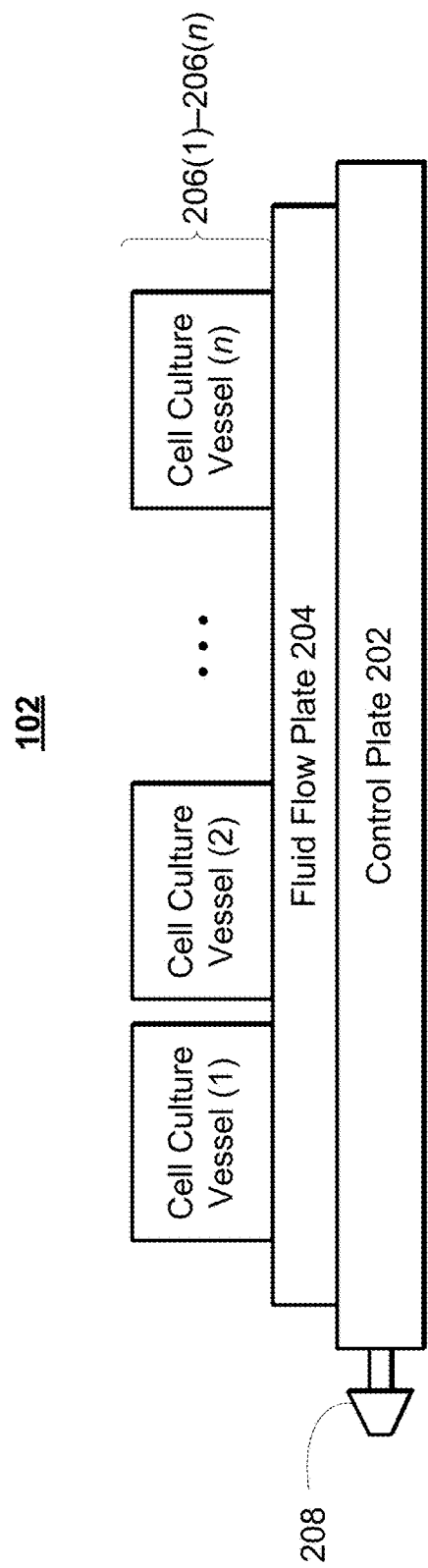
FIG. 2 illustrates a schematic of an example cell culture platform that can be used in the cell culture system of FIG. 1.

Referring now to FIG. 2, FIG. 2 is a schematic illustrating components of the cell culture platform 102. The individual components of the cell culture platform 102 are described in detail in relation to FIGS. 4-9. As a brief introduction, the cell culture platform 102 includes a control plate 202, a fluid flow plate 204, and a plurality of cell culture vessels 206(1)-(n). The fluid flow plate 204 is coupled to the control plate 202, and a plurality of cell culture vessels 206(1)-206(n) are coupled atop the fluid flow plate 204. The cell culture platform 102 further includes a plurality of fluid and/or gas inlet/outlet ports 208. As illustrated, the ports 208 are components of the control plate 202. In other implementations, the control plate 202, fluid flow plate 204, and/or cell culture vessels 206(1)-206(n) each include one or more ports 208.

Continuing the cell culture platform 102 overview, the cell culture platform 102 is used to culture cells and/or tissues. In some implementations, this includes the culture of multiple types of cells and/or tissue from different organ systems. In some implementations, as described below, the cell culture vessels 206 are configured to include 3-dimensional cell culture scaffolds to support and culture the cells and/or tissues. The remaining plates of the cell culture platform 102 facilitate interaction (e.g., fluidic communication) between the cells/tissues cultured within the cell culture vessels 206(1)-206(n), and enable the cell culture vessels 206 to be interconnected in physiologically meaningful ways.

In some implementations, the components of the cell culture platform 102 are reversibly coupled to one another. For example, the components of the cell culture platform 102 can be coupled to one another with claps, screws, via vacuum, adhesive or any combination thereof. In some implementations, the coupling element (e.g., a screw) that is used to couple the cell culture vessel 206 to the fluid flow plate 204 passes through the fluid flow plate 204 to also couple the fluid flow plate 204 to the control plate 202.

In certain implementations, one or more of the components of the cell culture platform 102 are disposable and/or reusable. For example, the control plate 202 may house control connections to the controller 112, sensor connections, actuators, custom components, or any combination thereof is intended to be reused with disposable fluid flow plates 204 and disposable cell culture vessels 206.

In some implementations, the disposable elements include passive structures that are produced using low-cost processes such as machining, injection molding, or embossing. In some implementations, these passive structures are controlled via actuators within the control plate 202. In some implementations, the control plate 202 provides a foundation to which disposable fluid flow plates 204 and cell culture vessels 206 may be modularly added.

Figure 3A:
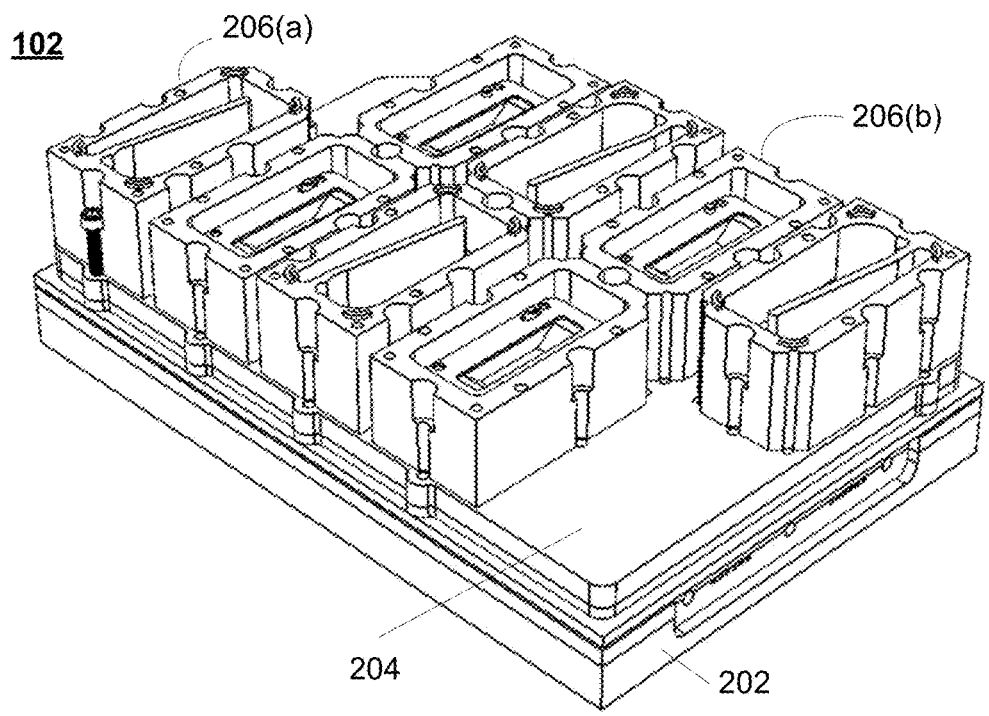
FIGS. 3A and 3B illustrate solid models of an example cell culture platform that can be used in the cell culture system of FIG. 1.

FIG. 3A is a solid model illustrating cell culture platform 102 in greater detail. As illustrated, eight cell culture vessels 206 are coupled to a fluid flow plate 204, which is, in turn, coupled to a control plate 202. The control plate 202 includes a first type of cell culture vessel 206(a) and a second type of cell culture vessel 206(b).

Figure 3B:
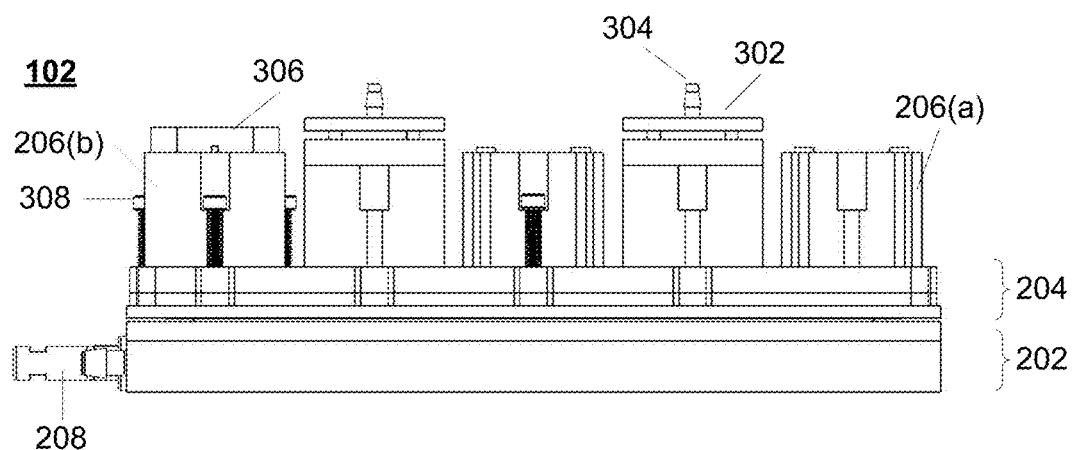

FIG. 3B is a side view of the model from FIG. 3A illustrating the cell culture platform 102. In some implementations, the cell culture vessels 206 are sealed with reversibly coupled lids 302 and 306. The lid 302 includes a port 304, which in some implementations, is used to flow gases and/or liquids into the cell culture vessel 206(b). The lid 306 is a sealed lid and does not include a port. As illustrated, the cell culture vessels 206 are coupled to the fluid flow plate 204 with screws 308.

Below, each of the control plate 202, the fluid flow plate 204, and the cell culture vessels 206 of FIGS. 2, 3A, and 3B are described in turn and in greater detail with reference to FIGS. 4-9.

As set forth above in reference to FIGS. 2, 3A, and 3B, the cell culture platform 102 includes a control plate 202. In general, the control plate 202 contains reusable connectors, actuators, and/or sensors that interface with the fluid flow plate 204 and/or cell culture vessels 206. In some implementations, the placement of the connectors, actuators and/ or sensors in the reusable control plate 202, provides a cost savings as portions of the cell culture platform 102 that directly interact with cells can be disposed of after experimentation, while the more expensive components can be reused. As described below, in some implementations, the control plate 202 is manufactured from a plastic or a multi-layer printed circuit board.

In some implementations, the control plate 202 includes between 5 and 10, between 10 and 30, between 30 and 50, between 50 and 100, or between 100 and 200 actuators. The actuators are used to control fluid flow through the fluid flow plate 204 and/or cell culture vessel 206, and, in some implementations, are used as pumps. The actuators control fluid flow by activating valves within the control plate 202, fluid flow plate 204 and/or cell culture vessel 206. In some implementations where the actuators are configured as pumps, they pump between about 100 nL and about 500 nL, between about 500 nL and 1000 nL, or between about 1000 nL and about 2000 nL/min of fluid through a channel. In other implementations, the pumps can cause flow rates of up to 480,000 nL/min. The flow induced by the actuator pumps can have a continuous, single shot, and/or reciprocating flow profile.

In some implementations, the pump is configured to inject a predetermined dosage of a toxin, test agent, medicaments (e.g., antibiotics, vaccines, biologics, and medical countermeasures), or any combination thereof into the fluid flow plate 204 and/or the cell culture vessel 206. For example, on a predetermined cycle (e.g., once per day, three times a day, once per hour, etc.) the pump-configured actuator may be configured to deliver an insulin dose to a cell culture vessel containing liver cells. In some implementations, a pump-configured actuator withdraws a predetermined fluid sample volume from the fluid flow plate 204 and/or the cell culture vessel 206. For example, the actuator may withdraw 100 nL from a cell culture vessel every hour, such that a medicament, analyte, or toxin, or other biologically relevant material concentration can be determined in the cell culture vessel.

In various implementations, the actuators are pneumatic actuators, electromagnetic actuators, valves, or a combination thereof. The mechanism of the actuator activation is described further in relation to FIG. 9A, and the mechanism of the actuator when acting as a pump to inject or withdraw fluid samples is described in relation to FIG. 9B. Briefly, the actuators include a membrane, which is driven by a piston. When activated, the actuator drives the piston and membrane into a channel placed above the actuator. The membrane shunts the flow of a fluid through the channel. In some implementations, pneumatic actuators are used because in some implementations, the activation of an electromagnetic actuator may induce heat or electromagnetic noise that may interfere with certain sensor applications such as transepithelial electrical resistance.

The actuators enable customized control of fluids through the cell culture platform 102. The use of a membrane in the actuator enables separation of biological liquids from the reusable components of the control plate 202. In some implementations, the flexible membrane used in the actuator (and/or pump structures) is manufactured from, but is not limited to, polyimide- and polyurethane-based materials. In some implementations, substantially the entire, or at least large portions of, the top surface of the control plate 202 is covered with the membrane.

In some implementations, the control plate 202 includes a fixed form factor that couples (or mates) with the cell culture vessel 206 and/or the fluid flow plate 204. As described below, fluid flow plate 204 and cell culture vessel 206 can be configured differently responsive to the needs of a given experiment. In these implementations, the standardized form factor of the control plate 202 enables the mixing and matching of other modular components to the control plate 202.

As introduced above, the control plate 202 includes one or more sensors 106 and/or sensor connections. For example, the control plate 202 can include flow meters, gas sensors, pH sensors, temperature sensors, transepithelial electrical resistance (TEER) sensors, or any combination thereof. In some implementations, the flow sensor is a thermal flow sensor. In certain implementations, the sensors 206 are mounted to polyimide substrates and separated from fluids by the above described membrane.

In implementations including sensor connections (or sensor expansion ports) the sensors 106 described herein are added to the control plate 202 based on the requirements of an experiment. For example, a researcher conducting a flow experiment may choose to only attach flow sensors to the control plate 202 and may forgo other sensors such as a pH sensor. In some implementations, removing sensors 106 by decoupling them from the expansion ports, facilitates the reusability of the control plate 202 by enabling delicate components of the control plate 202 to be removed prior to sterilization of the control plate 202. In some implementations, the sensor expansion ports are input/output ports for the controller 112, and allow for the connection of custom sensors to the control plate 202.

In some implementations, the control plate 202 includes at least one heating element. The heating element is employed to maintain a configurable temperature within one or more of the cell culture vessels 206. In some implementations, use of a heating element and closed cell culture vessels 206 enable experiments to be conducted without an incubator 104, as a predetermined microcondition can be maintained within each cell culture vessel 206.

In yet other implementations, the control plate 202 includes an auxiliary agent delivery module. The module connects to the control plate and enables specific agent dosage to one or more of the cell culture vessels 206.

To further describe the control plate 202 discussed above, FIGS. 4A-4C illustrate example implementations of the control plate 202. A person of ordinary skill in the art will recognize that features of the various control plates described below may be applied to any of the other control plates described herein.

Figure 4A:
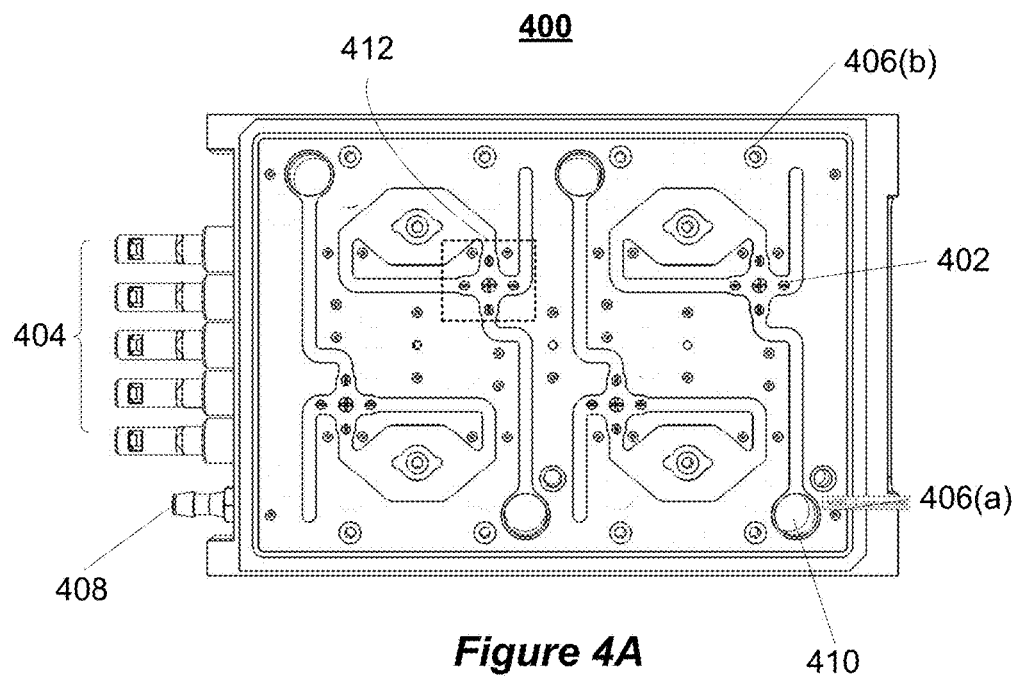
FIGS. 4A-4C illustrate solid models of example control plates that can be used in the cell culture system of FIG. 1.

FIG. 4A is a top view illustrating a pneumatic control plate 400. The control plate 400 includes a plurality of actuators 402 to act on flow channels within the fluid flow plate 204. The control plate 400 also includes a plurality of pneumatic ports 404 to control the plurality of actuators 402. The control plate 400 further includes a plurality of capacitor ports 410 that serve as fluidic capacitors, with a flexible valve or pumping membrane suspended across a port opening, the operation of which is discussed in more detail below. In addition, a vacuum inlet 408 is in fluid receiving communication with a plurality of vacuum ports 406 distributed across the control plate 400. In operation, after disposing the control plate 400 on the fluid flow plate 204, a suction can be applied to the vacuum inlet 108 and distributed through the vacuum ports 406. The control plate 400 may then suctionally engage the fluid flow plate 204 via the vacuum ports 406. In some implementations, mechanical clamps or fasteners (e.g., screws, clips, etc.) can be used to further strengthen the engagement of the control plate 400 to the fluid flow plate 204.

As described above, the control plate 400 includes a plurality of pneumatic actuators 402. As illustrated, control plate 400 includes twenty actuators divided into four 4-port, constant-volume pumps 412. Each constant-volume pump 412 corresponds to the intersection of two channels in the fluid flow plate 204. The actuator 402($a$) lies at the center of the constant-volume pump 412, and drives fluid (e.g., gas or liquid) through the four branches of the intersection. Each actuator 402($b$)-405($e$) controls the flow of the fluid into its respective branch of the intersection.

In some implementations, one or more of the capacitor ports 410 also serve as viewing ports. Viewing ports are pass throughs (or vias) that enable optical access to the dorsal side of the cell culture vessels 206 eventually coupled to the cell culture platform 102. In such implementations, some viewing ports may also serve as fluidic capacitors (e.g., may contain an optically transparent valve or pumping membrane), while other viewing ports are only viewing ports (e.g., do not contain a membrane). In some implementations, the control plate 400, fluid flow plate 204, and/or cell culture vessels 206 are manufactured from optically clear materials such that cell cultures are optically accessible without viewing ports. In some implementations, the components of the cell culture system 100 are substantially optically clear and include a plurality of viewing ports.

Figure 4B:
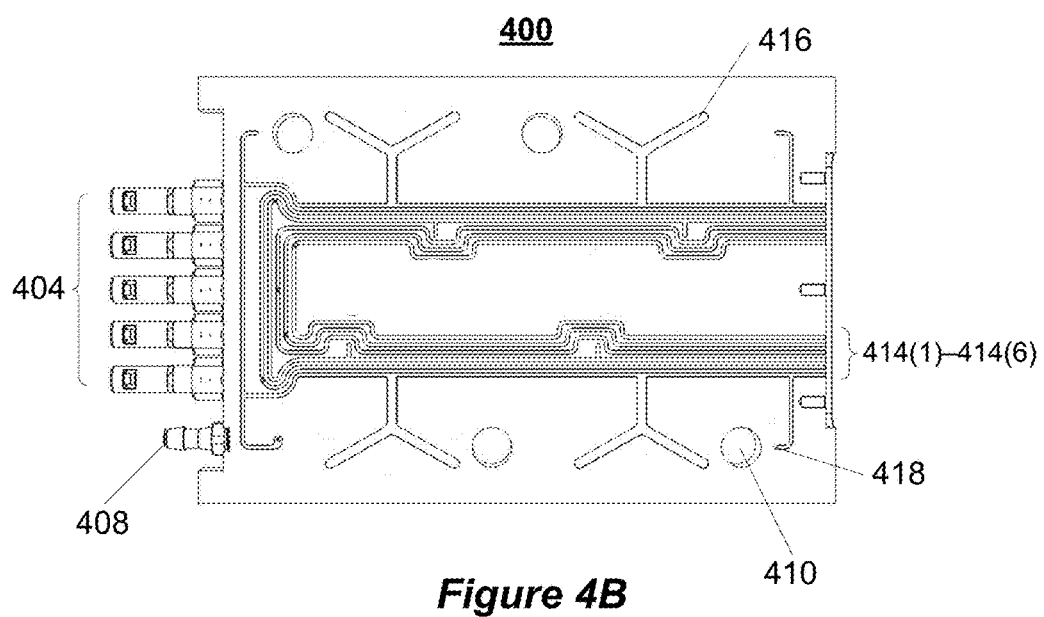

FIG. 4B is a cross sectional view illustrating the internal pneumatic flow channels of the control plate 400. As illustrated, the control plate 400 includes the channels 414(1)-414(6). The channel 414(1) corresponds the vacuum inlet 408. The channels 414(2)-414(6) each correspond to one of the pneumatic ports 404 and act as control channels for the above described actuators 402($a$)-402($e$). FIG. 4B illustrates that each constant-volume pump 412 is connected to the same control channels 414(2)-414(6), and thus operate in unison. In some implementations, each actuator 402 within constant-volume pump 412 of the control plate 202 is individually controllable.

The channel 414(1) includes a plurality of stems to route a fluid (e.g., a liquid or gas) to the vacuum ports 406. A first vacuum port 406($b$) includes a relatively larger diameter compared to a second vacuum port 406($a$). Accordingly, stem 416, which corresponds to the larger first vacuum port 406($b$), includes a larger diameter to support the increased flow through vacuum port 406($b$). In comparison, stem 418, which corresponds to vacuum port 406($a$) includes a relatively smaller diameter. In some implementations, the stems 416 and 418 and the fluid flow channels described herein have a diameter of about 1-5 mm, about 5-10 mm, and about 15-25 mm.

Figure 4C:
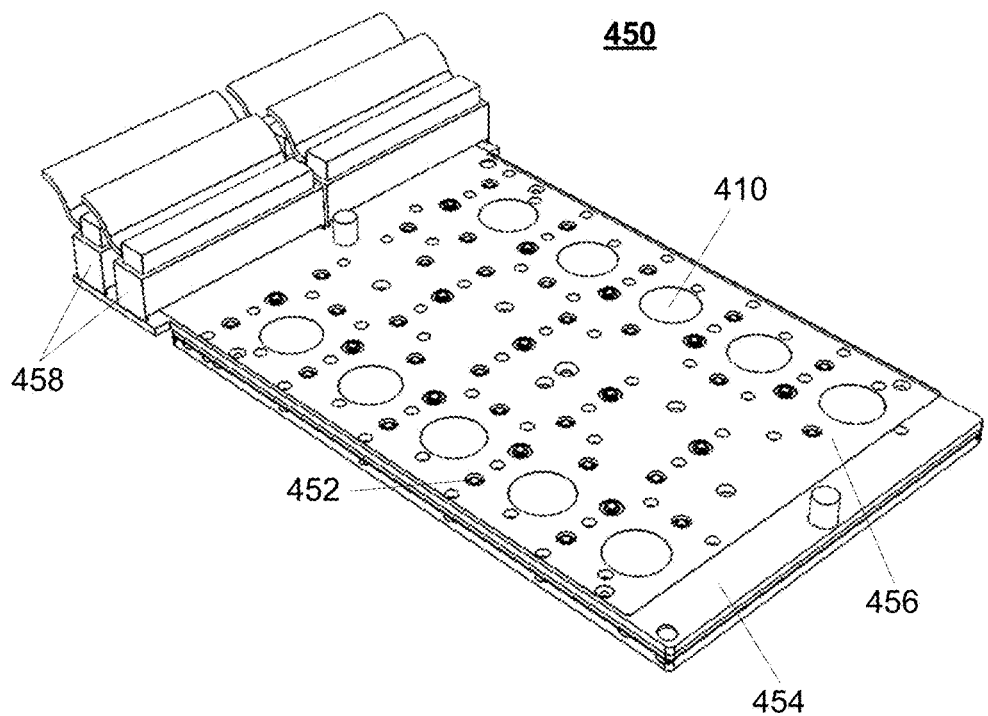

As described above, in some implementations, the actuator is an electromagnetic actuator. FIG. 4C is an isometric view of a control plate 450 with electromagnetic actuators 452. The control plate 450 is manufactured on a printed circuit board 454, and similar to control plate 400, includes a plurality of capacitor ports 410. Additionally, the control plate 450 includes a membrane 456 that protects the electronics of the control plate 450 from the fluids contained in the above layers. The membrane 456 also allows for a seal between the control plate 450 and the fluid flow plate 204 to protect the electronics from environmental moisture (e.g., humidity, for example in an incubator). The control plate 450 also includes a plurality of electrical connectors 458. As illustrated, control plate 450 does not include fluid flow channels.

In some implementations, the electromagnetic actuators enable a smaller relative footprint compared to the control plate 400. In some implementations, the actuators 452 are implemented for bi-stable operation with fixed mechanical stops for the pistons they incorporate. This enables the actuators to have reproducible stroke volumes and only require power during engaged-unengaged transitions. As suggested above, in some implementations, the control plate 400 with pneumatic actuators is used when it is desired to have no, or a reduced number of, electrical components within the cell culture platform 102. For example, if an experimenter is performing electro-physiological experiments and the electrical components of the control plate 202 interfere with the electrophysiology recordings, then the experimenter may choose to use a pneumatic based system.

The control plate 450 also includes a plurality of connectors 458. In some implementations, the connectors 458 are used to electrically couple the control plate 450 to the controller 112 for the purpose of activating the actuators 452. In other implementations, the connectors 458 are used to connect sensors 106 to the control plate 450 and ultimately to the control computer 110. In some implementations, pneumatic implementations also include connectors 458 for the connection of sensors 106.

Referring back to FIGS. 2, 3A, and 3B, the cell culture platform 102 includes a fluid flow plate 204. The fluid flow plate 204 includes a plurality of flow channels and pump chambers defined there through. The fluid flow plate 204 acts as an interface between the control plate 202 and the cell culture vessels 206. For example, the fluid flow plate 204 interfaces on its dorsal side with the actuators of the control plate 400. A fluid flow is then routed by the control plate 202 through the fluid flow plate 204 where the fluid can be routed to the cell culture vessels 206.

In some implementations, the fluid flow plate 204 is constructed from transparent, chemically stable, and mechanically robust thermoplastic materials such as polystyrene, polyetherimide, polyimide, polysulfone, or other similar materials. The material of the fluid flow plate 204 is selected to avoid chemical instabilities and chemical absorption.

In some implementations, dynamic control over flow through the fluid flow plate 204 is achieved using the above described actuators of the control plate 202. For example, the user can activate specific actuators to close, control the flow rate of, or route fluid away from channels.

In some implementations, the fluid flow plate 204 is disposable. In other implementations, the fluid flow plate 204 also includes actuators, sensors, and/or "reusable" components as described herein.

Figure 5A:
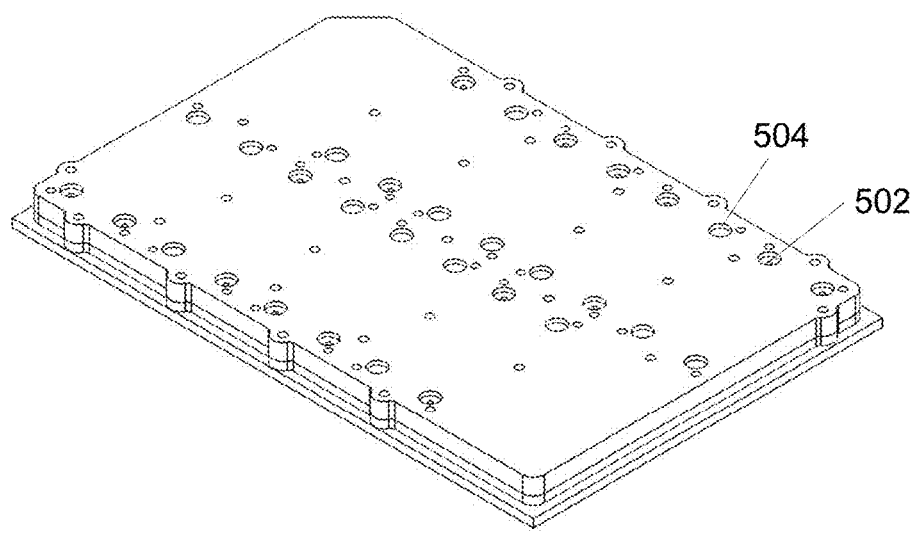
FIGS. 5A and 5B illustrate solid models of example fluid flow plates that can be used in the cell culture system of FIG. 1.

Now referring to FIG. 5A, which illustrates an isometric view of an example fluid flow plate 500. The top surface of the fluid flow plate 500 includes a plurality recesses (or mortises) 504. As described below, the cell culture vessels 206 include matching projections (or tenons). The mortises 504 and tenons interlock and properly align cell culture vessels 206 with the flow ports 502. As illustrated, the flow ports 502 are included in a subset of the mortises 504. In some implementations, each mortise 504 includes a flow port 502.

As illustrated, and referring back to FIGS. 3A and 3B, the fluid flow plate 500 supports six cell culture vessels 206. In some implementations, the fluid flow plate 500 supports between 1 and 10, 10 and 20, 20 and 50, 50 and 100 cell culture vessels 206.

Figure 5B:
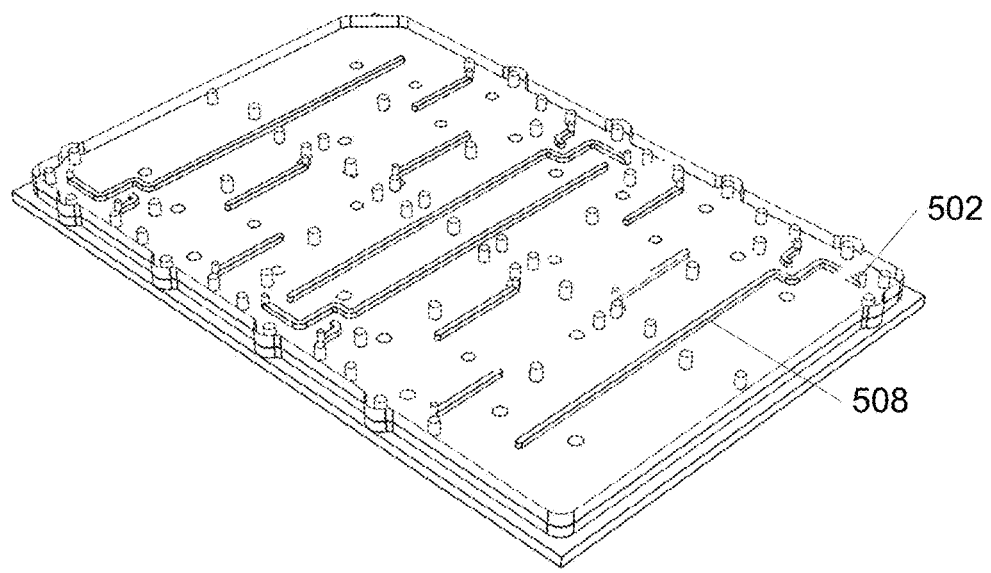

FIG. 5B illustrates a cross-sectional view of the fluid flow plate 500 from FIG. 5A. As revealed by the cross-sectional view, the fluid flow plate 500 includes a plurality of fluid flow channels 508. In some implementations, the fluid flow channels 508 connect one or more flow ports 502 to other fluid flow channels 508. Thus, in some implementations, the fluid flow channels 508 connect one or more cell culture vessels 206 and/or interconnect different portions of a single cell culture vessel 206. In some implementations, the fluid flow plate 500 includes a plurality of layers each of which include additional fluid flow channels 508. For example, the fluid flow plate 500 may include a first layer of fluid flow channels 508 that run along a first axis and a second set of fluid flow channels 508 that run orthogonal to the first axis.

Referring back to FIGS. 2, 3A, and 3B, the cell culture platform 102 includes a plurality of cell culture vessels 206(1)-(n), where n is the number of cell culture vessels. As described above, various cell culture platforms 102 can support between 1 and 10, between 10 and 20, between 20 and 50, or between 50 and 100 cell culture vessels 206. In some implementations, the cell culture vessels 206 are configured to house a specific cell type and/or cells from a particular organ type. In some implementations, the cells from the particular organ type include a plurality of cells types related to the particular organ. For example, when the cell culture vessel 206 is configured to house organ cells, the cell culture vessel can be configured to culture Loop of Henle thin segment cells, tubule cells, collecting duct cells, and glomerulus parietal cells. In some implementations with multiple cells types relating to a particular organ type, a first cell type related to the organ is cultured above a permeable membrane and a second cell type related to the organ is cultured below the permeable membrane.

In some implementations, the cell culture vessels 206 include a common exterior form factor regardless of the internal configuration of the cell culture vessel 206. For example, each cell culture vessel 206 can include the above described tenons and fluid ports at predetermined locations so the cell culture vessels 206 can be placed in any cell culture vessel slot on the fluid flow plate 202.

In some implementations, the cell culture vessels 206 are configured to support specific cell and/or organ tissue types. In some implementations, the cell culture vessels 206 may include specific scaffolds or structures to enable 3-dimensional cell growth of a specific cell and/or organ type. In other implementations, the cell culture vessels 206 are configured to support specific cell and/or organ tissue types by providing a predetermined flow rate to the cell culture vessel 206 and/or by providing predetermined fluids (e.g., specific media mixtures) to the cell culture vessel 206. For example, a cell type that requires a high shear force can be cultured in a cell culture vessel 206 with a plurality of input ports and a plurality of output ports. The plurality of input and output ports enable a relatively larger volume of fluid to flow through the cell culture vessel 206, thus imparting a relatively larger shear force on the cells within the cell culture vessel 206. In some implementations, cells that require little or no shear force may be cultured in cell culture vessels with a single port, such that nutrients diffuse into the cell culture vessel through the single port under no force from a fluid flow.

In other implementations, based on their physiological requirements, cells are cultured in a scaffold submerged in media or on a membrane at an air-liquid interface. For example, alveolar cells from the lung may be placed in a cell culture vessel 206 that is designed to provide air to the top-side of the cells while supplying the dorsal side of the cells with nutrients. In another example, liver cells may be cultured on a permeable membrane above a reservoir such that diffusion can occur through the liver cell layer and membrane to the reservoir.

As described in greater detail below, in some implementations, the cell culture vessels 206 include slots for one or more cell culture inserts. The cell culture inserts house the cells cultured in the cell culture vessel 206. The cell culture inserts are removable and enable the individual cultures to be seeded and grown outside of the cell culture system 100. For example, a company may sell pre-seeded cell culture inserts, which a researcher purchases and then inserts into a cell culture system 100.

In some implementations, the cell culture vessels 206 include multiple compartments that are separated by semi-permeable membranes. In some implementations, the membranes can include specific matrix components representing the surface chemistry, mechanical stiffness, and porosity of in vivo tissues. In some implementations, cells are cultured directly on the membranes.

As with the other components of the cell culture platform 102, in some implementations, the cell culture vessels 206 are disposable. The cell culture vessels 206 are manufactured from optically transparent materials such as polystyrene and/or polyimide. The cell culture vessels 206 materials are stable and compatible with cell culture and biological fluids relative to conventional microfluidic materials. For example, in some implementations, the cell culture vessels 206 are manufactured from PDMS. In some implementations, disposable cell culture vessel components are manufactured from thermoplastics such as polystyrene, polycarbonate, cyclic olefin copolymer (COC), or any combination thereof. In some implementations, the cell culture vessels 206 are manufactured by direct machining, embossing, injection molding, or any combination thereof may be used. In some implementations, the control plate 202 and/or fluid flow plate 204 are manufactured through similar processes with similar materials to those described above.

In some implementations, the cell culture vessels 206 and/or the fluid flow plate 204 include one-way valves. The one-way valves enable the cell culture vessels 206 to be temporally removed from the fluid flow plate 204 during experimentation. For example, a user may remove a cell culture vessel 206 from the cell culture platform 102 to perform a separate experiment or test on the cells within the removed cell culture vessel 206.

In some implementations, the above described fluid reservoir 118 and/or waste reservoir 120 can have the same form factor as a cell culture vessel 206, enabling the fluid reservoir 118 and/or the waste reservoir 120 to be modularly added to the cell culture platform 102. The fluid flow plate 204 and the control plate 202 can then flow growth media or other fluids (such as a medication or toxin) from the reservoir to the other components of the cell culture platform 102.

As described below, in some implementations, the cell culture vessels 206 include customized scaffold structures for each physiological system model. In some implementations, the scaffolds (also referred to as cell culture inserts) enable individual models to be developed separately from the cell culture platform 102 and then supplied individually for practical implementation.

In some implementations, specialized drug storage and delivery may be required for specific cell culture vessels 206 (e.g., delivering insulin to a cell culture vessel 206 culturing liver cells). These implementations can include custom modules fitted to the above described lids of specific culture wells. For example, and referring to FIG. 3B, the port 304 on lid 302 may be used to enable delivery of an agent to the interior of cell culture vessel 206(b). In some implementations, the delivery module is controlled by the control plate 202 and/or directly by the controller 112.

FIGS. 6A-6D illustrate schematics of various example cell culture vessels. As illustrated, each cell culture vessels 600, 610, 620, and 630 includes an inlet port 602 and an outlet port 604. In some implementations, the cell culture vessels include a plurality of inlet ports 602 and/or a plurality of outlet ports 604. In certain implementations, each port of a cell culture vessel 206 is configured to be an inlet port 602 or an outlet port 604 by configuring the fluid flow plate 204 with the one or more actuators in the control plate 202.

Each cell culture vessel 600, 610, 620, and 630 also includes a cell culture insert 606. As described above, the cell culture insert 606 enables the off-platform culturing of cells. The cell culture vessels include slots which secure the cell culture inserts 606 in place. In some implementations, the bottom surface of the cell culture insert includes a semi-permeable membrane on which cells are cultured.

FIG. 6A illustrates a cell culture vessel 600 configured for a basal flow 608. As described above, some cells are responsive to specific flows and/or shear forces. For example, a cell population of liver cells may more closely mimic in vivo liver cells if exposed to a shear force. By employing a cell culture insert 606 with a permeable membrane, the configuration of cell culture vessel 600 exposes a cell's basal membrane to a flow and thus the described shear force. In some implementations, a basal flow allows the dorsal surface to be exposed to gases. For example, this type of configuration may be used to mimic alveolar tissue. In this example, alveolar epithelial cells are cultured in the cell culture insert 606. Nutrients are supplied to the cells through the basal flow 608, as the cells are exposed to gas along their top surface.

FIGS. 6B and 6C illustrate cell culture vessels 610 and 620, respectively. The cell culture vessels 610 and 620 are configured to provide a top flow. The cell culture vessel 610 includes a raised cell culture insert 606. The raised cell culture insert 606 enables diffusion through the cells and into a reservoir space 611 located beneath the insert 606(b). In some implementations, the cell culture configuration of cell culture vessel 620 is used to culture gut epithelial cells. FIG. 6D illustrates the cell culture vessel 630. The cell culture vessel 630 is configured to allow flow above and below the cell culture insert 606.

Figure 7A:
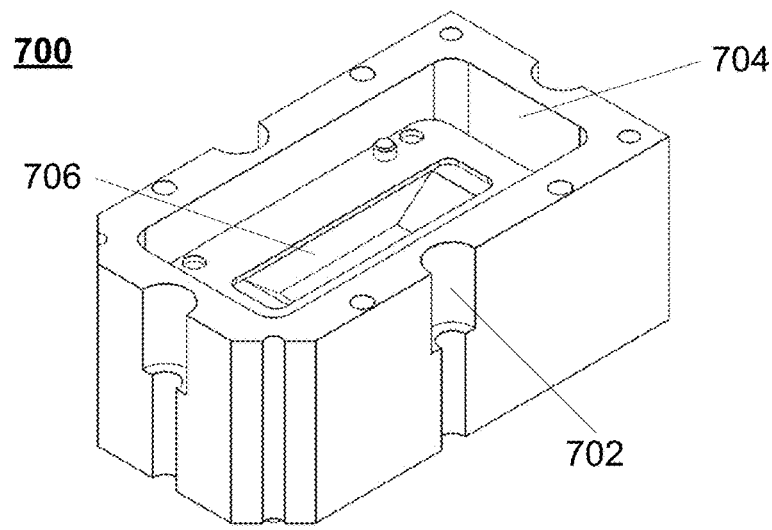
FIGS. 7A and 7B illustrate solid models of an example cell culture vessel.

FIG. 7A illustrates an isometric view of one example implementation of a cell culture vessel 630, similar to the cell culture vessel 206(b) in FIG. 3A. Exteriorly, each wall of the cell culture vessel 700 includes a recess used to secure the cell culture vessel 700 to a fluid flow plate 204 with thumb-screws. The interior of the cell culture vessel 700 includes a top flow area 704 and cell culture area 706. In some implementations, the floor of the cell culture area 704 is a semi-permeable membrane.

Figure 7B:
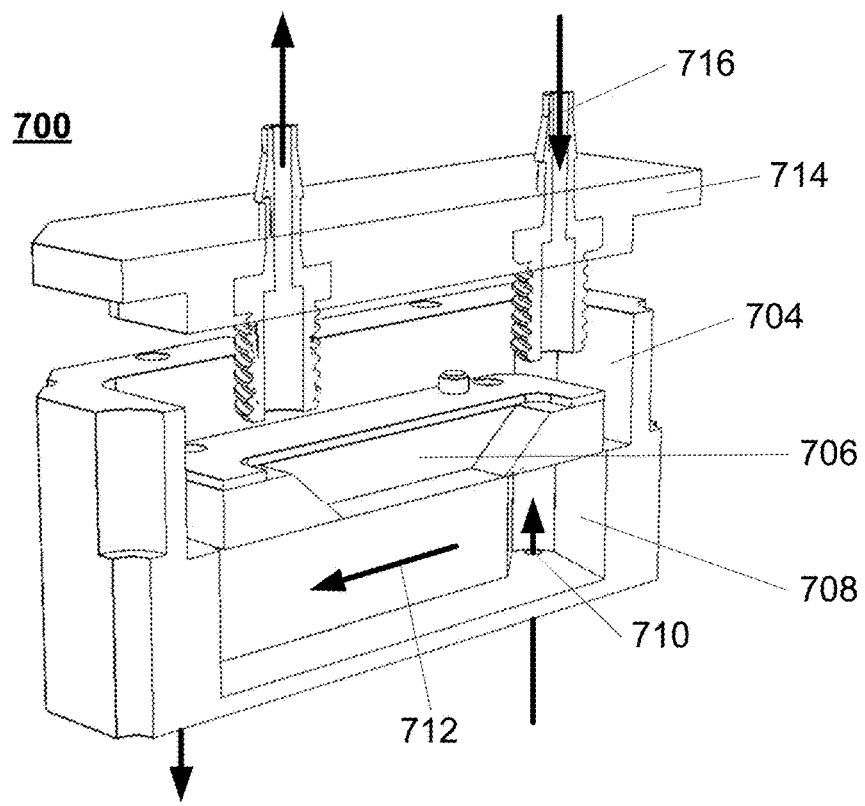

FIG. 7B illustrates an isometric cutaway view of the cell culture vessel 700. As revealed by the cut-a-way, the cell culture vessel 700 includes a lower flow area 708. Fluid flows into and out of the lower flow area 708 through ports 710. The arrow 712 illustrates one possible flow pattern through the cell culture vessel 700. A lid 714 is optionally coupled to the cell culture vessel 700. The lid 714 is manufactured with similar materials as the cell culture vessel 700. The lid 714 allows gas exchange but maintains sterility similar. In some implementations, the lid 714 is transparent to provide optical access to the cells within the cell culture area 706. The lid 714 also includes a plurality of access ports 716. In some implementations, the access ports 716 are used to introduce a gas and/or a liquid into the top flow area 704. The gas and/or liquid is supplied to the access ports 716 through the control plate 202 and/or the fluid flow plate 204 in some implementations. In other implementations, the gas and/or liquid supply to the access ports 716 is independent of the cell culture platform 102. In some implementations, the cell culture vessel 700 is used to culture lung tissue. For example, lung cells are cultured within the cell culture area 706. Nutrients in the lower flow area diffuse to the cells through the semi-permeable membrane of the cell culture area 706. Gas, emulating gas within a human's lungs, is passed into the top flow area 704 through the access ports 716.

Figure 8:
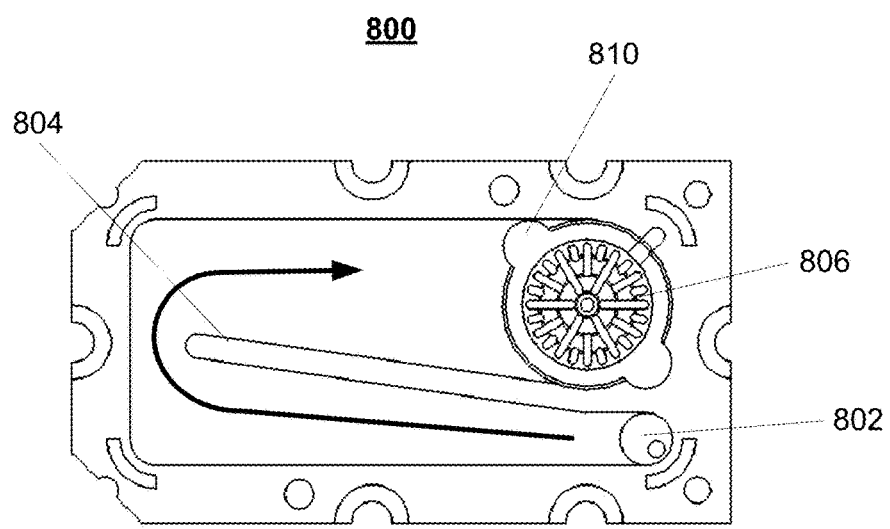
FIG. 8 illustrates a solid model of an example cell culture vessel.

FIG. 8 illustrates another implementation of a cell culture vessel 206. FIG. 8 illustrates a top view of cell culture vessel 800, similar to the cell culture vessel 206(a) in FIG. 3A. The cell culture vessel 800 includes an inlet port 802. The fluid flow entering the cell culture vessel 800 is directed around a wall 804 and toward an outlet 806. The outlet 806 is recessed within a slot 808, which is similar to above described slots for securing the cell culture inserts. In the cell culture vessel 800, a portion of the fluid flow flows through the cells and membrane of the cell culture insert to reach the outlet 806. Recesses 810 enable excess fluid to bypass the cell culture insert and flow directly to the outlet 806. In some implementations, a cell culture vessel similar to the cell culture vessel 800 is used for culturing cells, such as liver cells, in the presence of a shear force.

Figure 9A:
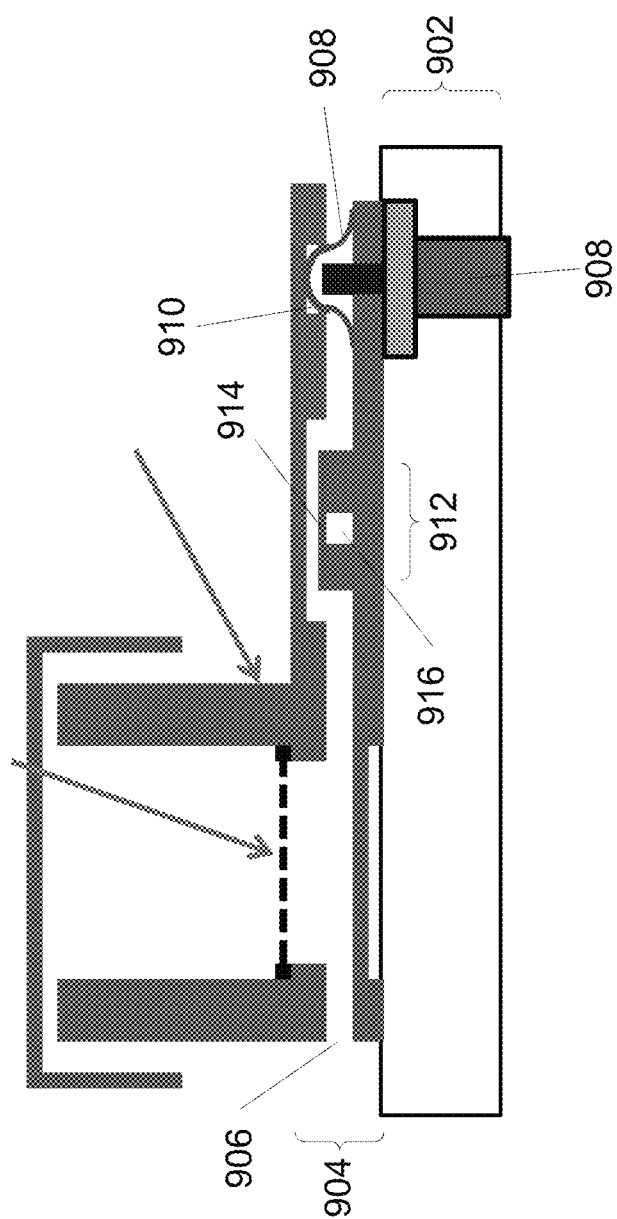
FIG. 9A illustrates a schematic of an example actuator that can be used in the cell culture system of FIG. 1.

FIG. 9A illustrates a cross sectional view of an actuator 900 suitable for inclusion in the control plate 202 for controlling fluid paths in the fluid flow plate 204. The actuator 900 is housed within control plate 902. A fluid flow plate 904, which includes the flow channel 906, is coupled to the control plate 902. To close the flow channel 906, the actuator 900 drives its piston upward. As described above, a membrane 908 separates the actuator from the fluid of the fluid flow plate 904. Once deployed the piston drives into a recess 910 in the top of the flow channel. This creates a seal, closing the channel 906.

FIG. 9A also illustrates a fluidic capacitor 912. In some implementations, one or more fluidic capacitors 912 are included in the flow channels of the cell culture platform 102. The fluidic capacitor 912 smooths a fluid flow through the channel to which it is attached. The fluidic capacitor 912 includes a membrane 914 above a cavity 916. Responsive to a pulsatile wave (or other non-smooth flow) the membrane 914 deforms into the cavity 916. The expansion of the channel into the cavity 916 slows the pulsatile wave and smooths the flow through the channel.

Figure 9B:
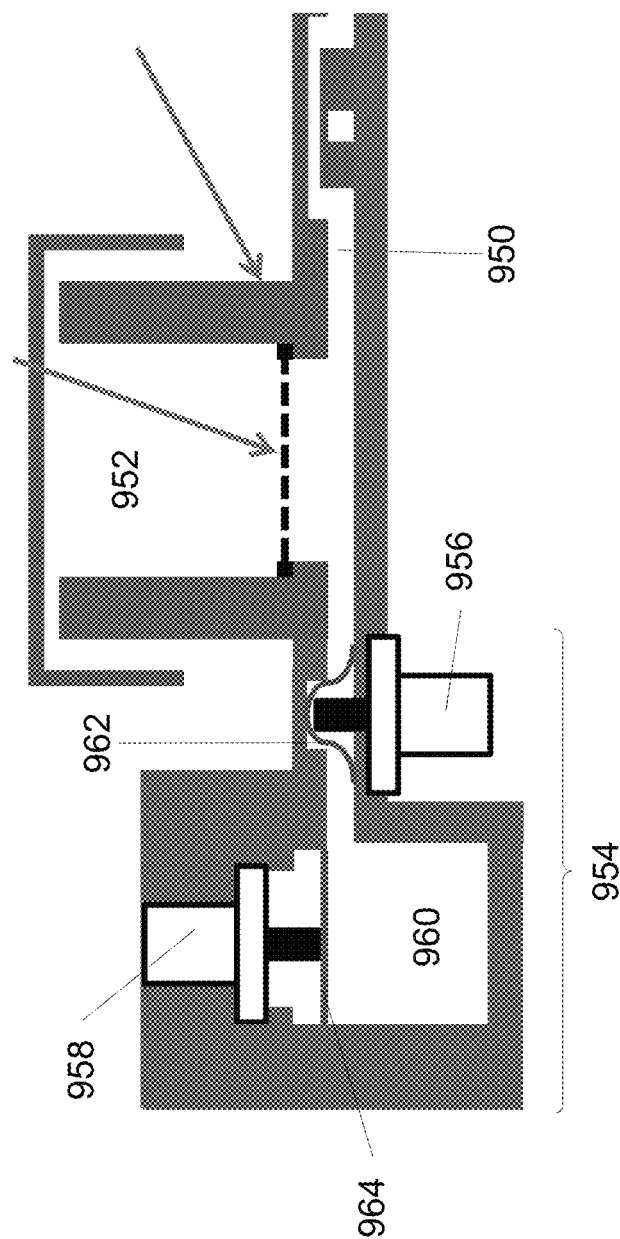
FIG. 9B illustrates a schematic of an example implementation of an actuator configured to inject and withdraw fluid samples that can be used in the cell culture system of FIG. 1.

FIG. 9B illustrates a cross sectional view of example actuators configured to inject and/or withdraw fluid samples for a cell culture system. As illustrated in FIG. 9B, a fluid channel 950 runs below a cell culture vessel 952. An injection/withdrawal (I/W) module 954 is coupled to one end of the channel 950. The I/W module 954 includes a first actuator 956, which when activated seals the I/W module 954 off from the fluid channel 950. The mechanism of the first actuator 956 is similar to the above described actuator 908 illustrated in FIG. 9A. Briefly, the first actuator 956 drives a membrane 962 into a recess in the top of the fluid channel 950, which creates a seal and closes the I/W module 954 off from the fluid channel 950. The I/W module 954 also includes a second actuator 958, which is coupled to a second membrane 964. The I/W module 954 also includes a reservoir 960 to store a fluid for injection and/or after withdrawal. In some implementations, the I/W module 954 also includes an access port (not illustrated) to enable the injection and/or withdrawal of fluid from the reservoir 960.

To withdraw (also referred to as sipping) a sample from the fluid channel 950, the first actuator 954 lowers. With the first actuator 954 lowered, a fluid can enter the I/W module 954. The second actuator 958 retracts its piston, and drives the second membrane 964 upward. The upward movement of the membrane 964 creates a vacuum in the reservoir 960, which draws a fluid from the fluid channel 950 into the reservoir 960. To inject a fluid into the fluid channel 950, a similar process occurs. During a fluid injection, the second actuator 958 extends its piston, creating a pressure build up in the reservoir 960. Responsive to the first actuator 956 opening access to the fluid channel 950, the pressure build up drives the fluid in the reservoir 960 out of the I/W module 954 and into the fluid channel 950.

In some implementations, the I/W module 954 does not require the second actuator 958 to withdraw fluid from the fluid channel 950. For example, the flow present in the fluid channel 950 may drive fluid into the reservoir 960. In some implementations, the I/W module 954 is a component of the above described fluid flow plate, cell culture vessels, or control plate. For example, the I/W module 954 may be a component of a cell culture vessel and inject or withdraw fluid directly from the cell culture vessel. In other implementations, the I/W module 954 is a separate module form the cell culture platform, and may be modularly added to any of the cell culture vessels and/or the fluid flow plate.

Figure 10:
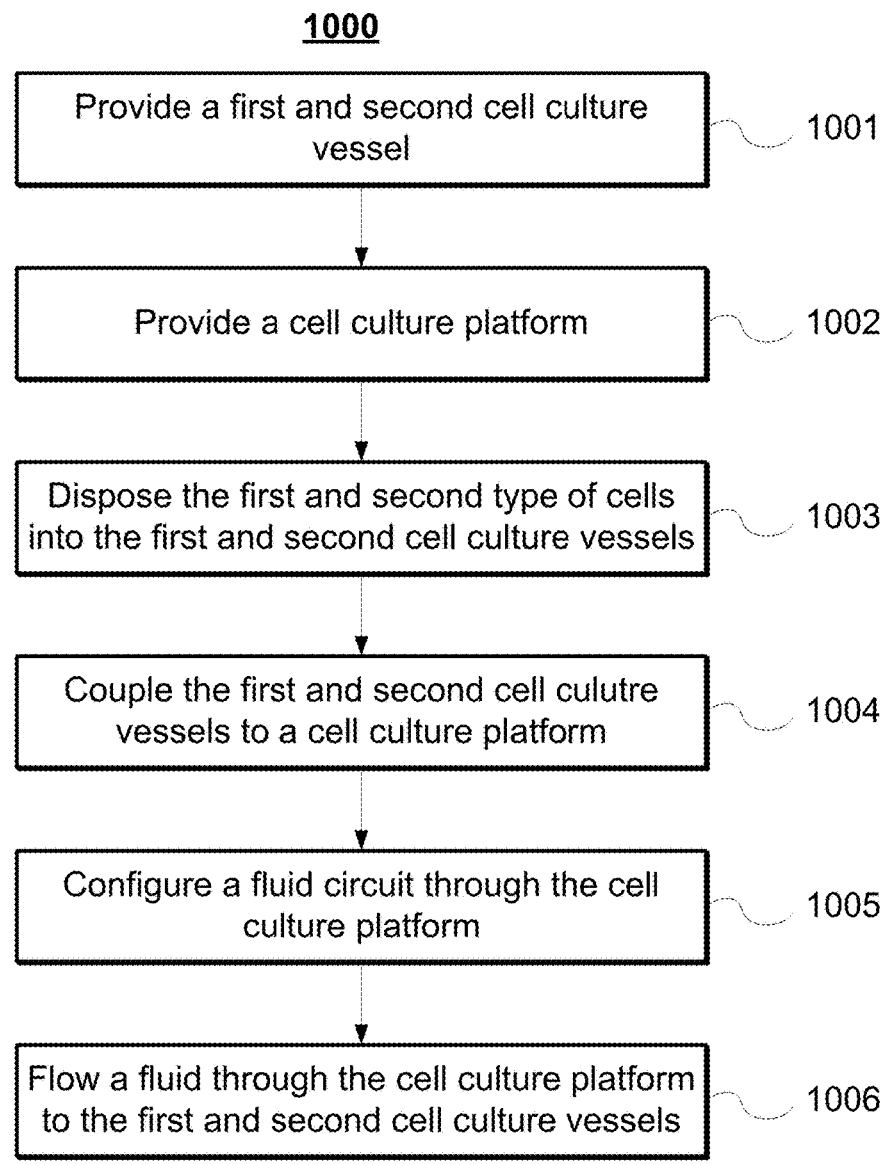
FIG. 10 illustrates a flow chart of an example method for culturing cells in the cell culture system of FIG. 1.

FIG. 10 illustrates a flow chart of a method 1000 for culturing a plurality of cells. In some implementations, the method 1000 is used to test the interplay of organ systems in vitro. The method 1000 includes providing a first and second cell culture vessel (step 1001). The method 1000 also includes providing a cell culture platform (step 1002). Cells of a first type are disposed in the first cell culture vessel and cells of a second type are disposed in the second cell culture vessel (step 1003). Then, the cell culture vessels are coupled to the cell culture platform (step 1004) and a fluid path (also referred to as a fluid circuit) is configured to the first and/or second cell culture vessels (step 1005). The method 1000 also includes flowing a fluid through the cell culture platform to the first and second cell culture vessels (step 1006).

As set forth above, the method 1000 begins with the provision of a first and second cell culture vessel (step 1001) and cell culture platform (step 1002). The first and second cell culture vessels can be similar to the cell culture vessels described above in relation to FIGS. 2-3B, and 6A-8. In some implementations, the first and second cell culture vessels are configured differently. For example, the first cell culture vessel can be configured to culture tissue from a first organ (e.g., lung tissue), and the second cell culture vessel can be configured to culture tissue from a second organ (e.g., liver tissue). For example, the first cell culture vessel may be the cell culture vessel 700 illustrated in FIG. 7A and the second cell culture vessel may be the cell culture vessel 800 illustrated in FIG. 8. In some implementations, the cell culture platform is the cell culture platform 102 discussed above. In some implementations, one or more cell culture vessels are already coupled to the cell culture platform 102 prior to the beginning of the method 1000.

Next, a first type of cells is disposed in the first cell culture vessel and a second type of cells are disposed in the second cell culture vessel (step 1003). In some implementations, the cell culture vessel configurations selected in step 1001 is responsive to the type of cells a user intends to use in step 1003. In some implementations, a user is able to mimic an organ system by combining a specific cell type with a specific cell culture vessel configuration. For example, a user may select to combine alveolar cells with a cell culture vessel configuration that provides a liquid-gas interface (e.g., the cell culture vessel 700 illustrated in FIGS. 7A and 7B).

In some implementations, the first and second cell types are different cell types. In these implementations, a user may combine different cell types and cell culture vessel configurations to mimic a plurality of organ systems. In some implementations, the organ systems correspond to two or more of a liver, a lung, or a kidney. As described below, in some implementations the modular combination of multiple organ systems enables a user to study the interactions between those organ systems. In other implementations, a user can use a cell culture platform culturing a plurality of interconnected organ systems to study drug dosing and drug uptake.

Next, the first and second cell culture vessels are coupled to the cell culture platform (step 1004). In some implementations, as described above in relation to FIGS. 2-3B, the cell culture vessels are coupled to a fluid flow plate, which acts as an interface between a control plate and the cell culture vessels. In some implementations, the cell culture vessels are reversibly coupled to the control plate and/or fluid flow plate.

The method 1000 further includes configuring a fluid circuit between the first and second cell culture vessels (step 1005). As described above, in some implementations, an actuator is coupled to (or within the control plate). Activation of the actuator controls at least one valve in the fluid flow plate and/or cell culture vessels. By activating the one or more actuators in the cell culture platform, a user configures a fluidic circuit that routes the fluid flow between the first and second cell culture vessels.

Responsive to coupling the first and second cell culture vessels to the control plate, a fluid is flowed through the cell culture platform to the first and second cell culture vessels (step 1006). In some implementations, the fluid enters the cell culture platform at an interface with the fluid flow plate. In yet other implementations, the fluid enters the cell culture platform through one or more of the cell culture vessels. In some implementations, flowing the fluid through the cell culture platform constitutes recirculating the fluid through the cell culture platform. In some implementations, the fluid is a growth medium, blood, a gas, or any combination thereof.

In some implementations, the method 1000 further includes disposing a third cell type into a third cell culture vessel and then coupling the third cell culture vessel to the cell culture platform in addition to or in place of the first and second cell culture vessels. In other implementations, the method 1000 also includes reconfiguring the fluid circuit created in step 1006 by activating one or more actuators. For example, by activating one or more of the actuators, the above described fluid circuit can be reconfigured to include the third cell culture vessel. In other implementations, the method 1000 includes rearranging and/or removing the first, second, and/or third cell culture vessels within the cell culture platform. In yet other implementations, the method 1000 includes measuring a parameter within the cell culture platform 102. For example, a temperature in one of the cell culture vessels and/or a flow rate through the fluid circuit may be measured. In some implementations, a cell culture vessel is temporally removed from the cell culture platform 102 to perform the measurement. In other implementations, a cell culture vessel is permanently removed and replaced with a cell culture vessel housing similar or different cells or organ tissue type.

One of ordinary skill in the art will recognize that in some implementations the above method steps of the method 1000 may be performed in a different order or one or more of the method steps may be omitted. For example in one implementation, the fluid circuit may be configured prior to the coupling of the cell culture vessels to the cell culture platform. In a similar example, a user may purchase a fluid flow plate that includes preconfigured fluid flow channels and therefore does not have to be configured once coupled to the cell culture platform.

Figure 11:
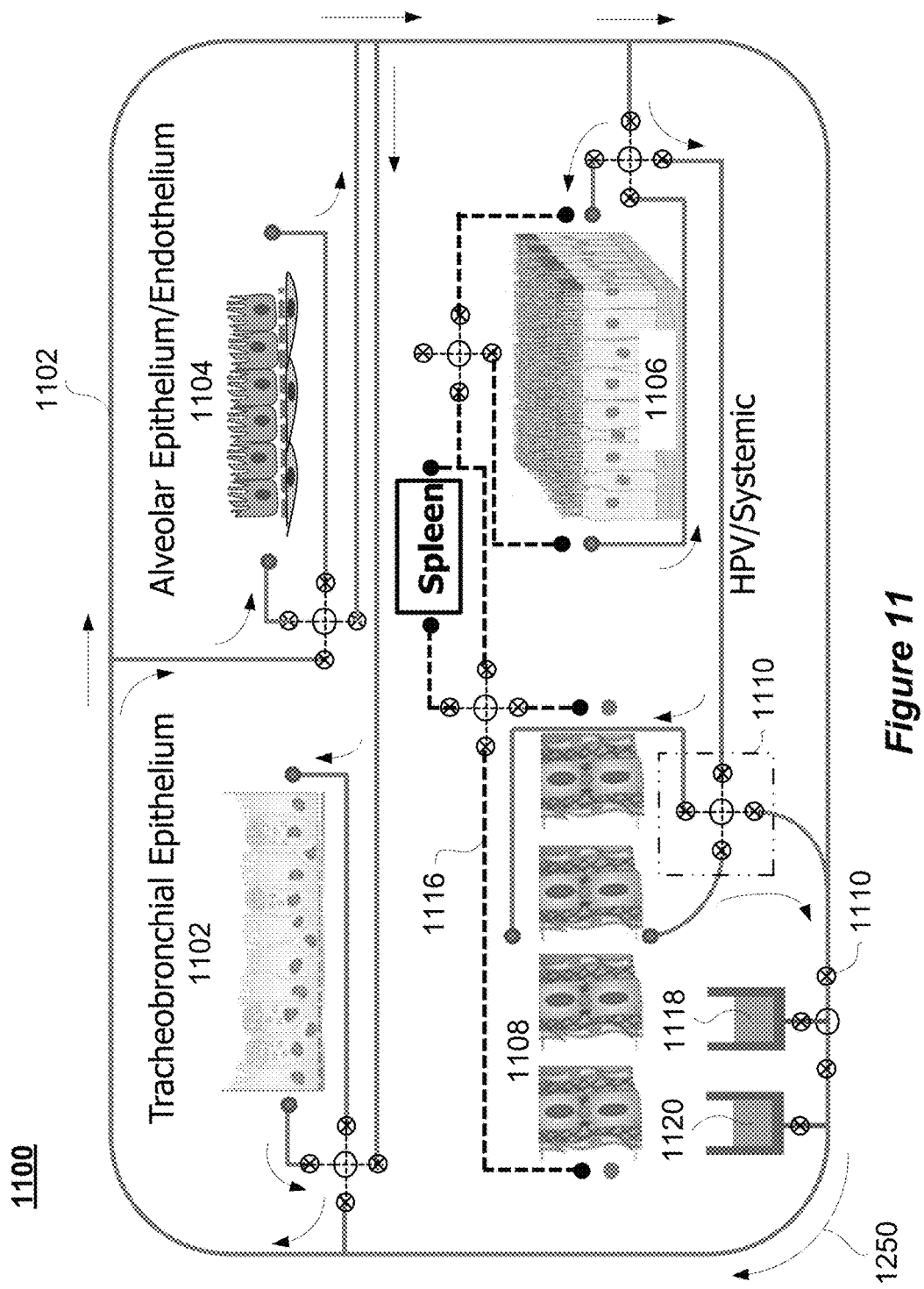
FIG. 11 illustrates a schematic of an example use case for the cell culture system of FIG. 1.

FIG. 11 illustrates an example schematic of a use case of the above described system. The schematic illustrates a system 1100 that, in some implementations, is used to investigate drug candidates. The system 1100 corresponds to a cell culture platform culturing cells that correspond to four organ systems. In some implementations, one or more cell culture vessels correspond to each organ system. The four organ systems of the system 1100 include tracheobronchial tissue 1102, alveolar tissue 1104, small intestine tissue 1106, and liver tissue 1108. Using the plurality of valves 1110 and constant-volume pumps 1112, which correspond to actuators in a control plate, two circulatory circuits are created within the fluid flow plate used to implement the system 1100. The first circuit 1114 represents a circulatory (or cardiovascular) system. The first circuit 1114 provides nutrients to each of the organ systems 1102, 1104, 1106, and 1108. In some implementations, the fluid used in the transport of nutrients and other chemicals to each of the organ systems 1102, 1104, 1106, and 1108 is a growth medium, blood, or a blood analyte. The second circuit 1116 (illustrated as a dashed line) is coupled to only the small intestine tissue 1106 and the liver tissue 1108. The second circuit 1116, small intestine tissue 1106, and liver tissue 1108 correspond to a lymphatic system and filter waste and other materials from the first circuit 1114.

In the system 1100, each of the cell culture vessels used to implement the system 1100, provide a top flow and a bottom flow, similar to the cell culture vessel 630 illustrated in FIG. 6D. For example, in the cell culture vessels corresponding to the alveolar tissue 1104 and the tracheobronchial tissue 1102, the cells are provided nutrients through fluid from the first circuit 1114, which flows through the lower chamber of the cell culture vessels. In the top chamber of the cell culture vessels, the alveolar tissue 1104 and the tracheobronchial tissue 1102 are exposed to oxygen. Exposure to oxygen on one side and the fluid of the first circuit 1114 on the other, enables the cells of the alveolar tissue 1104 and the tracheobronchial tissue 1102 to oxygenate the fluid while also removing $CO_2$.

The bottom flows in the cell culture vessels, which correspond to the small intestine tissue 1106 and the liver tissue 1108, also originate from the first circuit 1114. As described above, fluid from the first circuit 1114 is used to supply the respective tissue with nutrients. In the cell culture vessels that correspond to the small intestine tissue 1106 and the liver tissue 1108, the top flow is a component of the flow from the second circuit 1116. In addition to receiving nutrients from the fluid of the first circuit 1114, the small intestine tissue 1106 and the liver tissue 1108 filter the fluid of the first circuit 1114 and transfer the filtered waste to the fluid of the second circuit 1116, where it can be removed from the system 1100.

By culturing organ specific tissue types within a biomimetic environment (e.g., within a cell culture vessel as described above wherein the temperature, humidity, and other parameters mimic in vivo conditions) and interconnecting each of the organ systems in a physiologically meaningful way, experiments can be conducted on in vitro cells that substantially mimic the responses of in vivo cell populations. For example, a predetermined dose of a drug can be introduced to the system 1100 through the drug delivery system 1120. Starting at the drug delivery system 1120, the first circuit 1114 of the system 1100 transports the drug to each of the organ systems 1102, 1104, 1106, and 1108. The arrows 1250 illustrate the path taken by drug through the first circuit 1114. The cells uptake the drug as it flows through the first circuit 1114. Additionally, some of the drug is filtered out of the fluid of the first circuit 1114 as it circulates through the system 1100. For example, the alveolar tissue 1104 may remove some of the drug as an off gas when the alveolar cells remove $CO_2$ from the fluid of the first circuit 1114. The liver tissue 1108 may also filter the drug out of the fluid of the first circuit 1114 and then transfer the drug to the fluid of the second circuit 1116.

As the drug flows through the system 1100, a number of measurements can be made. For example, a user may monitor the pH of the fluid in the first circuit 1114 to determine if the drug is causing the fluid to become basic or acidic. A user may sample the waste collected in the fluid of the second circuit 1116 to determine if the drug dosage is too high. For example, a user may perform experiments wherein the drug dosage is lowered to the point where the drug is substantially not present in the fluid of the second circuit 1116. In some implementations, a substantial amount of drug in the fluid of the second circuit 1116 indicates that too much drug is being introduced into the system 1100.

In some implementations, the user may temporally remove one of the cell culture vessels corresponding to one of the tissue systems and examine the cells in the cell culture vessel with the above described microscope. For example, the user may examine the cells with a microscope to determine if the drug is causing damage to the cells. In some implementations, the user can examine cells within a cell culture vessel without removing the cell culture vessel from the cell culture platform.

FIGS. 12A and 12B are cross-sectional illustrations of two configurations of a valve assembly 1200, according to an example arrangement. The valve assembly 1200 may be incorporated to mate with one or more active elements within fluid channels of a cell culture platform, such as the cell culture platform 102 shown in FIGS. 1-3B. For example, the valve assembly 1200 can be used to implement any of the valves included within the fluid flow plate 204 or valves 1110 shown in FIG. 11. The valve assembly 1200 includes a spring 1212, an electromagnet 1214, a washer 1216, a valve head 1218, a valve membrane 1220, and a layer stack 1222.

The layer stack 1222 includes a plurality of bonded or laminated layers that form a microfluidic structure defining a path for a fluid flow 1224 from an inlet portion at a first end and an outlet portion at a second end. The fluid flow 1224 may be subject to changes in fluid pressure sufficient to change the direction of the fluid flow (e.g., from the inlet portion to the outlet portion, or from the outlet portion to the inlet portion), and as such, the fluid flow 1224 may be bidirectional in operation. That is, in some implementations, under some operating conditions, the inlet may serve as an outlet and the outlet may serve as an inlet. In some implementations, the layer stack 1222 may form the fluid flow plate 204 of a cell culture platform 102.

The layer stack 1222 may additionally define features configured to interact with other components of the valve assembly 1200, such as a valve seat 1223 configured for operative engagement with the valve membrane 1220 to block the fluid flow 1224 through the layer stack 1222 (e.g., to prevent the fluid flow 1224 from reaching the outlet portion at the second end). The layers in the layer stack 1222 may be formed from materials including, and without limitation, polyimide, polyetherimide, poly(methyl methacrylate), polycarbonate, cyclic olefin copolymer, and other polymers typically used in microfluidic devices. The layers may be bonded (e.g., via plasma treatment) or laminated using adhesives (e.g., phenolic butyrol, R/flex® 1000, acrylic-based adhesives, urethane-based adhesives, or silicone-based adhesives) or hot pressing (e.g., thermal bonding). The valve membrane 1220 is layered on top of the layer stack 1222 in between the valve head 1218 and the valve seat 1223. The space between the valve membrane 1220 and the valve seat is referred to herein as the "valve cavity." In various implementations, the valve membrane 1220 may be formed as one or more thin layers (e.g., with a thickness of about 25 microns or less) of polyimide- and polyurethane-based materials or biocompatible metals (e.g., titanium, stainless steel, cobalt, tantalum, etc.). In some implementations, the biocompatiable material is biostable and non-corroding. In one arrangement, the valve membrane 1220 is a polyimide layer with a thickness of between about 12 to about 50 microns. In some arrangements, the valve membrane 1220 has a resting tensile strain characteristic (e.g., between 0.25 and 2.0%). For such arrangements, during manufacture of the valve assembly 1200, the valve membrane 1220 may be stretched or pulled until a desired resting tensile strain characteristic is met, and then applied and bonded to a top surface of the layer stack 1222.

The spring 1212 is operatively coupled at its distal end (i.e., the end of the spring located closer to the layer stack 1222) to the valve head 1218 and the washer 1216. The spring 1212 is configured to bias the position of the valve head 1218 toward the valve seat 1223. The spring 1212 may be implemented as any of various biasing elements, such as coil springs, leaf springs, air springs, and so on. In the arrangement shown, the spring 1212 is provided as a coil spring formed of an elastic and/or shape memory material (e.g., spring steel). The valve head 1218 is coupled to the terminal end of the spring 1212 at the distal end, and is formed to complement the shape and size of the valve seat 1223 to selectively provide a fluid seal. The washer 1216 is a plate of magnetically-responsive material annularly disposed about and coupled to the spring 1212 adjacent to the valve head 1218. The spring 1212 is movably disposed through the electromagnet 1214, and the electromagnet 1214 is disposed adjacent to the washer 1216. The electromagnet 1214 is configured to selectively generate a magnetic field in response to an electrical input. In particular, electromagnet 1214 is configured to magnetically attract and engage the washer 1216 upon receiving the electrical input.

In operation, the valve assembly 1200 selectively switches between an open configuration 1210 and a closed configuration 1230. In the open configuration, an electrical input is provided to the electromagnet 1214, which magnetically attracts and engages the washer 1216. The washer 1216 in turn compresses the spring 1212, drawing the valve head 1218 away from the valve seat 1223 and out of the valve cavity. As such, the fluid flow 1224 may pass from the inlet portion, through the valve seat 1223, to the outlet portion of the layer stack 1222. In the closed configuration, no electrical input is provided to the electromagnet 1214, and therefore there is little or no magnetic attraction between the electromagnet 1214 and the washer 1216. The spring 1212 presses the valve head 1218 into the valve membrane 1220, pressing the valve membrane 1220 into the valve cavity and into contact with the valve seat 1223. The engagement of the valve membrane 1220 to the valve seat 1223 blocks the fluid flow 1224 from reaching the outlet portion of the layer stack 1222. Additional features and arrangements of the valve assembly 1200 are discussed below.

Figure 13A:
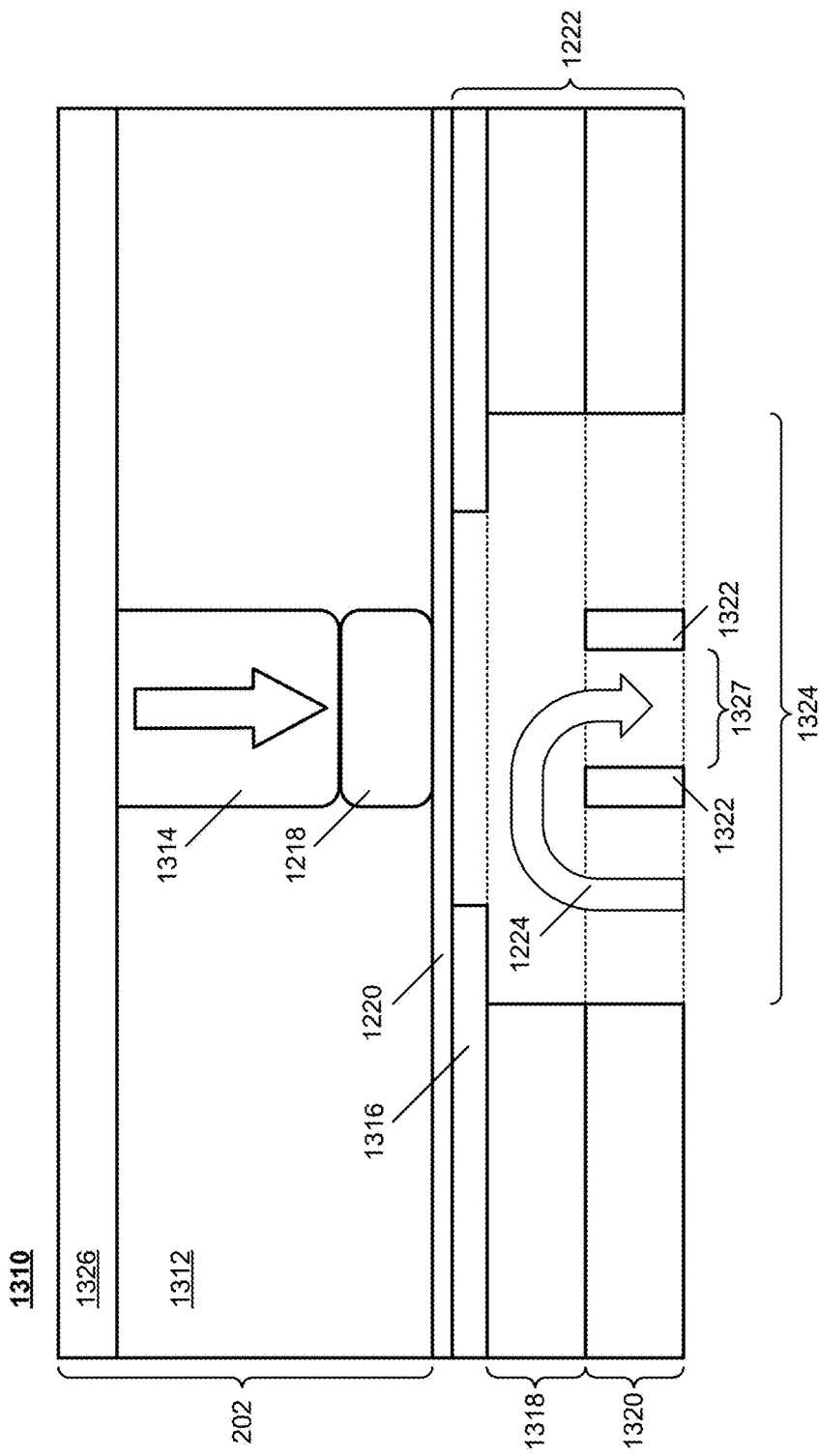
FIG. 13A is a schematic diagram of a second valve assembly incorporating a stress reduction layer.

FIG. 13A is a schematic diagram of a second valve assembly 1310 incorporating a load distribution layer 1316, according to an example arrangement. The second valve assembly 1310 includes an actuator 1314, the valve head 1218, the valve membrane 1220, and an arrangement of the layer stack 1222. Similar to the spring 1212 and electromagnet 1214 of the valve assembly 1200, the actuator 1314 is a structure configured to selectively apply pressure through the valve head 1218 to the valve membrane 1220 to block the fluid flow 1224 from flowing through the second valve assembly 1310. Fluid flow 1224 is blocked by the valve head 1218 forcing the valve membrane 1220 into a valve cavity (formed between the valve membrane 1220 and a valve seat 1322 within the layer stack 1222) and into contact with the valve seat 1322. However, in contrast to the valve assembly 1200, in the second valve assembly, the actuator 1314 may be biased such that the valve head 1218 is in an open position in an off state, and actuation of the actuator 1314 causes the valve assembly to enter a closed state.

In some arrangements, the actuator 1314 is included within the control layer 202 of a cell culture platform, such as the cell culture platform 100, and may be disposed within a vacuum chamber 1312 defined by a valve head facing surface of the valve membrane 1220 and a surrounding airtight housing 1326. In some arrangements, the airtight housing 1326 may include portions of the control plate 202. In such arrangements, fluid (e.g., gas) may be evacuated from the vacuum chamber 1312 via one or more fluid channels coupled to the vacuum chamber 1312 (e.g., via a vacuum pump communicatively coupled via one or more ports of the control plate 202 to the fluid channels coupled to the vacuum chamber 1312) to reduce and maintain the fluid pressure therein (e.g., to ½ to ¼ atmospheres). In some such arrangements, the fluid pressure in the vacuum chamber 1312 may be lower than the fluid pressure in a fluid passage 1324 defined by the layer stack 1222. As a result of the pressure differential across the valve membrane 1220, the valve membrane 1220 may be biased toward the vacuum chamber 1312 and distend into the vacuum chamber 1312 (i.e., toward the valve head 1218) in the absence of pressure provided by the actuator 1314. In turn, upon an application of pressure from the actuator 1314, the valve head 1218 may press the valve membrane 1220 into the valve cavity and into contact with the valve seat 1322. In other arrangements, the pressure differential across the valve membrane 1220 may provide a restorative force on the valve membrane 1220 in operation. In such arrangements, the pressure differential may bias the valve membrane 1220 back to a flat resting position (i.e., as shown in FIG. 13A) after the actuator has been turned off. In some implementations, the existence of a vacuum in the vacuum chamber 1312 can be used instead of a spring to return the valve membrane 1220 to an open position, away from the valve seat 1322. In some implementations, the restoring force of the vacuum may be used in conjunction with a spring.

In the second valve assembly 1310, the layer stack 1222 includes the load distribution layer 1316, a support layer 1318, and a valve seat layer 1320. The layers of the layer stack 1222 include cutout portions that, when bonded or laminated together, define the valve cavity in the fluid passage 1324 discussed above. The valve seat layer 1320 includes cutouts that define a portion of the fluid passage 1324, a valve seat 1322, and an outlet 1327. In operation, the actuator 1314 causes the valve head 1218 to press the valve membrane 1220 and edge portions of the load distribution layer 1316 into the valve cavity to close the valve by engaging the valve membrane 1220 to the valve seat 1322. In some arrangements, the valve seat 1322 has a resting tensile strain characteristic (e.g., as discussed with respect to the valve membrane 1220, above) to prevent or reduce delamination from an underlying layer during construction or operation.

The support layer 1318 is disposed on top of the valve seat layer 1320 and includes at least one cutout above the valve seat 1322 that defines another portion of the fluid passage 1324. The load distribution layer 1316 is a flexible layer (e.g., an elastic or elastomeric layer) sandwiched between the valve membrane 1220 and the support layer 1318, and includes at least one cutout configured to reduce stress concentrations and spread bending loads imposed on the valve membrane 1220 over the course of operation. The cutout of the load distribution layer 1316 is sized (e.g., between about 2.5 mm and about 3.0 mm in diameter, measured from one edge of the load distribution layer 1316 cutout to an opposite edge of the cutout) to be smaller than the cutout of the support layer 1318 (e.g., about 3.2 mm in diameter, measured from one edge of the support layer 1318 cutout to an opposite edge of the cutout). The cutout in the load distribution layer 1316, in some implementations, is centered above the valve seat 1322. As such, when the valve head 1218 presses into the valve membrane 1220 toward the valve seat 1322, the unsupported portions of the load distribution layer 1316 flex along with the valve membrane 1220, thereby providing an increased bend radius at the unsupported edges of the valve membrane 1220 as the valve membrane 1220 distends toward the valve seat 1322. In contrast, in the absence of the load distribution layer 1316, valve membrane 1220 stress may be more acutely concentrated at the cutout edges of the support layer 1318 as the valve membrane 1220 distends toward the valve seat 1322.

In various implementations, a load distribution layer similar to the load distribution layer 1316 and/or a vacuum chamber similar to the vacuum chamber 1312 shown in FIG. 13A can be incorporated into the various other valve assembly configurations discussed herein, without departing from the scope of the disclosure.

Figure 13B:
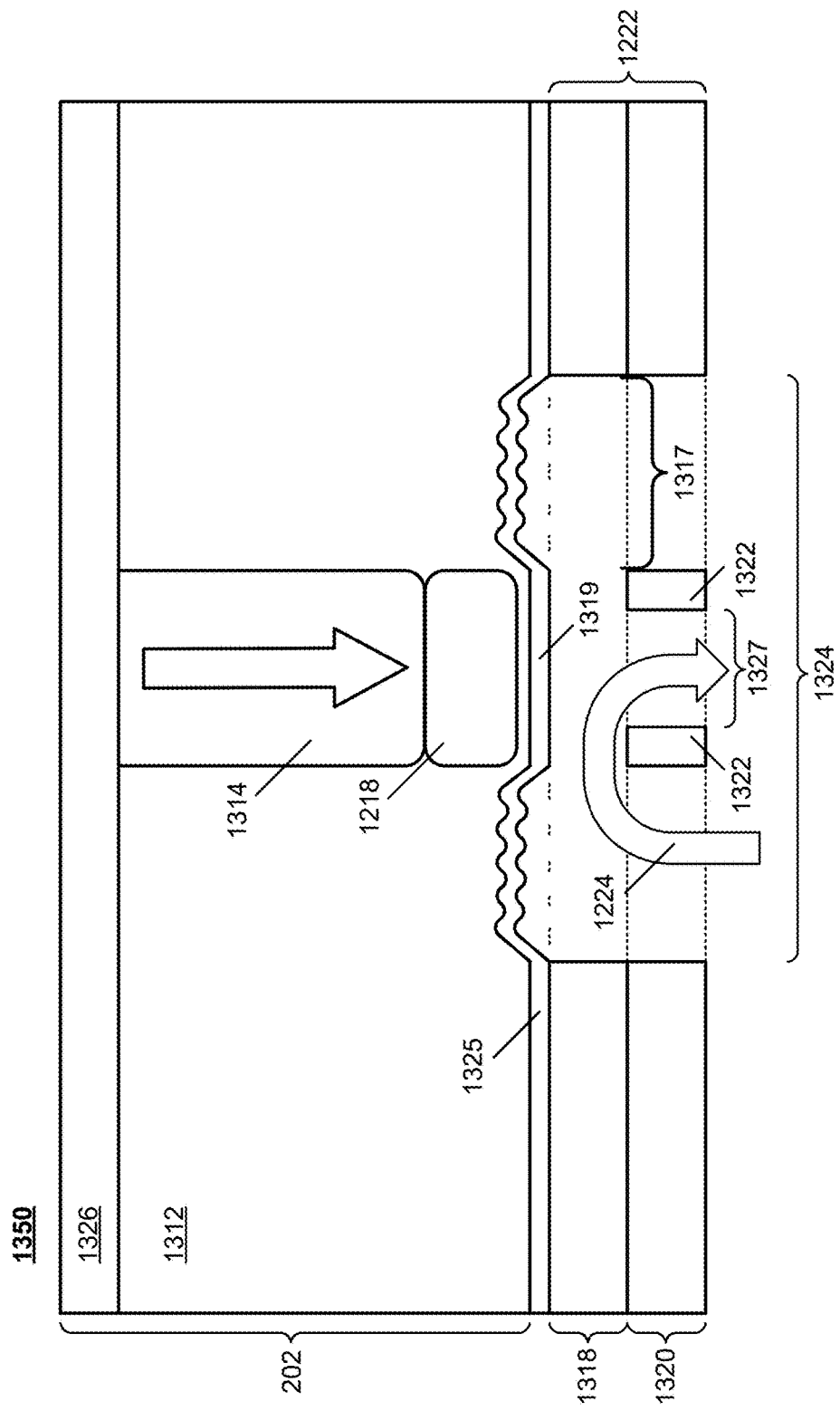
FIG. 13B is a schematic diagram of a second valve assembly incorporating a corrugated valve membrane.

FIG. 13B is a schematic diagram of a third valve assembly 1350 incorporating a corrugated valve membrane 1325, according to an example arrangement. Similar to the second valve assembly 1310, the third valve assembly 1350 includes a vacuum chamber 1312, an actuator 1314, a valve head 1218, and a layer stack 1222 including a support layer 1318 and a valve seat layer 1320. However, in lieu of the load distribution layer 1316 and the valve membrane 1220 of the second valve assembly 1310, the corrugated valve membrane 1325 is disposed on top of the support layer 1318. In some implementations, the third valve assembly, can also include a load distribution layer, similar to the load distribution layer 1316 between the corrugated valve membrane 1325 and the support layer 1318. As with the previously discussed valve assemblies, the space between corrugated valve membrane 1325 and the valve seat included in the valve seat layer 1320 is referred to as the valve cavity. The corrugated valve membrane 1325 includes a plurality of corrugations to relieve operational stress. In some arrangements, the corrugated valve membrane 1325 includes concentric corrugations disposed above the cutout portion 1317 of the support layer 1318 and annularly about a flat portion 1319 of the corrugated valve membrane 1325. The flat portion 1319 of the corrugated valve membrane 1325, in some implementations, is centered above, and has a diameter that is about the same as the outer diameter of the valve seat 1322. In some implementations, the diameter of the flat portion 1319 is greater than the outer diameter of the valve seat 1322. In some implementations the flat portion 1319 has a thickness which is greater—in some implementations, several times greater—than the thickness of the corrugated section to limit bending of the flat portion. The corrugations may be formed in the corrugated valve membrane 1325 via embossing, plastic deformation, or molding. In some arrangements where the corrugated valve membrane 1325 is formed of metal, the corrugations may be formed via electroforming or stamping. In some arrangements, the corrugated valve membrane 1325 may include between about two and about ten corrugations between the flat portion 1319 and the outer edge of the in the support layer 1318. In addition, in various arrangements, the depth of each corrugation may be less than a maximum deflection of the corrugated valve membrane 1325, for example, ranging from less than about 100 microns to about 300 hundred microns. In operation, upon an application of pressure by the valve head 1218 on the flat portion 1319 of the corrugated valve membrane 1325, the flat portion 1319 of the sinusoidal valve membrane 1325 is displaced towards the valve seat 1322. Instead of the membrane stretching to accommodate the displacement, the corrugations in the sinusoidal valve membrane 1325 can expand through bending outward at their respective corners. Thus, the load on the sinusoidal valve membrane 1325 in such implementations can be predominantly in the form of a bending load instead of a stretching load (as would be imposed on the valve membrane 1220 shown in FIGS. 12A-13A. Expansion through bending can require less force than bending through distension. Moreover, certain membrane materials may be more susceptible to damage from distension than from bending. Additionally the corrugation structure may be designed to reduce maximum bending stress particularly at the edge of the cutout 1318 where maximum bending stress may be expected in the absence of corrugations. Accordingly, implementations including a corrugated valve membrane 1325 may be more durable. While FIG. 13B shows corrugations having a generally sinusoidal shape, in other implementations, the corrugations may have other profiles, such as a saw-toothed or triangular profile, a square-waved or rectangular profile, a semicircular or other arcuate profile. In addition, while only shown specifically in FIG. 13B, it is understood that the membranes shown in the other valve assemblies discussed herein can be replaced with a corrugated valve membrane without departing from the scope of this disclosure.

Figure 14:
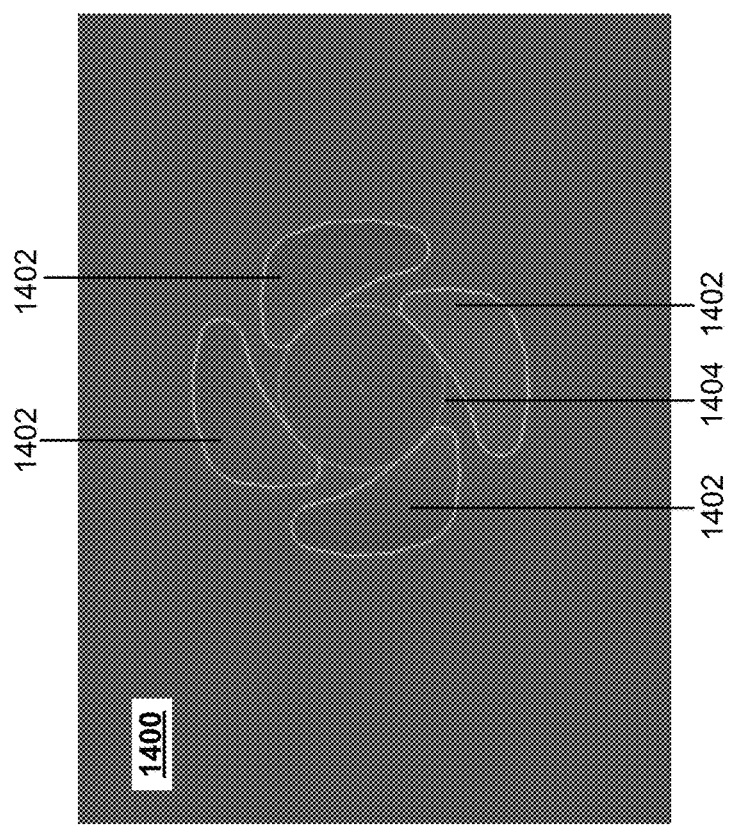
FIG. 14 is an illustration of an elastomer layer.

FIG. 14 is an illustration of an elastomer layer 1400, according to an example arrangement. In various arrangements, the elastomer layer 1400 may be included in valve assemblies as part of a valve membrane and/or portions of layer stacks. For example, the elastomer layer 1400 may be used as or disposed on one or more of the valve membrane 1220, valve seat layer 1320, the load distribution layer 1316, and support layers 1318 (e.g., any of the other layers of the layer stack 1222). Incorporation of one or more instances of the elastomer layer 1400 may provide improved conformance of the valve membrane to respective valve seats and improve valve assembly wear characteristics. In addition, incorporating elastomers into valve assemblies may provide for tighter seals and therefore lower leak rates in operation. The elastomers may be selected to minimize adsorption and absorption of fluid media constituents comprising fluid flows through valve assemblies. In some implementations, the elastomer layer 1400 may be formed of various fluorosilicones, Viton®, or fluoropolymer elastomers (e.g., Kalrez®). In various implementations, the elastomer layer can have a thickness ranging between about 0.25 mm and about 0.5 mm.

In addition, in various arrangements, the elastomer layer 1400 may include additional features configured to improve durability and operational efficiency of associated valve assemblies, such as lateral relief cutouts 1402 and an anti-stiction coating 1404. The lateral relief cutouts 1402 are cut out sections of the elastomer layer 1400 corresponding to portions surrounding a footprint of the valve head 1218 and/or the valve seat 1322 (e.g., around those surfaces where the valve head 1218 and/or the valve seat 1322 directly or operatively engages the elastomer layer 1400). The lateral relief cutouts 1402 are configured to reduce the amount of elastomer material at those portions of valve assemblies that may be subject to bending load or strain (e.g., distending portions of the valve membrane 1220, portions of the valve seat layer 1320 adjacent to the valve seat 1322). As a result, lateral relief cutouts 1402 may reduce the net stiffness and increase the elasticity of the elastomer layer 1400 at specific locations in an associated valve assembly. For example, where the elastomer layer 1400 is coupled to the valve membrane 1220, the lateral relief cutouts 1402 may provide increased elasticity at portions of the valve membrane 1220 subject to distension. As another example, where the elastomer layer 1400 forms the valve seat layer 1320, the lateral relief cutouts 1402 may prevent delamination of the valve seat 1322 during fabrication or operation. In various arrangements, the lateral relief cutouts 1402 leave portions of the elastomer layer 1400 that connect an intact center portion (e.g., corresponding to the location of a footprint of a valve head 1218) to the rest of the elastomer layer 1400.

The anti-stiction coating 1404 is a thin coat or film (e.g., between about 5.0 and about 50.0 nanometers thick) of stiction-reducing material on an external face of the elastomer layer 1400 that may be subject to periodic physical contact with another component of an associated valve assembly. For example, the valve membrane 1220 may be subject to periodic contact with the valve head 1218 at a first side, and/or periodic contact with the valve seat 1322 at a second side. In turn, the valve seat 1322 may be subject to periodic contact with the second side of the valve membrane 1220. The anti-stiction coating 1404 may be applied to any of these interface footprint surfaces to reduce stiction upon contact. The anti-stiction coating 1404 may be formed of various types of stiction-reducing materials such as, for example, titanium, aluminum, gold, platinum, or chrome, or metal oxides such as alumina or titania. Organic anti-stiction coatings are also possible (e.g. fluoropolymer coatings). The anti-stiction coating 1404 may be added to the elastomer layer 1400 via evaporation, atomic layer deposition, or sputtering. In some arrangements where the anti-stiction coating 1404 is made up of gold or platinum, an attachment layer formed of titanium or chrome may be used between the anti-stiction coating 1404 and the elastomer layer 1400 to promote adherence. In some arrangements, the anti-stiction coating 1404 is formed as a metal coat that is about 10.0 nanometers thick.

Figure 15:
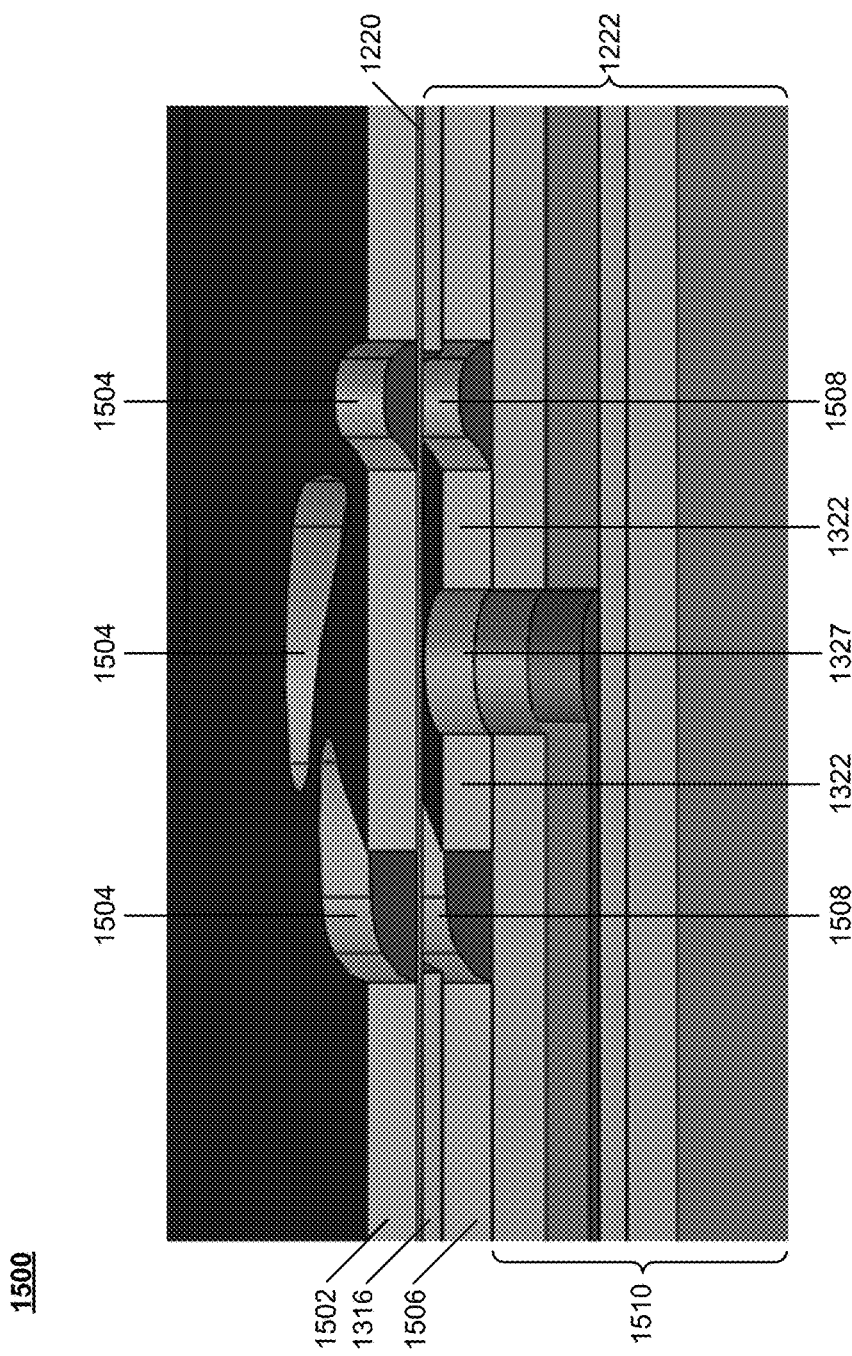
FIG. 15 is a cross-sectional illustration of a third valve assembly.

FIG. 15 is a cross-sectional illustration of a fourth valve assembly 1500, according to an example arrangement. The fourth valve assembly 1500 includes a first elastomer layer 1502, the valve membrane 1220, and an arrangement of the layer stack 1222. The first elastomer layer 1502 is disposed on top of a first side of the valve membrane 1220 (i.e., disposed toward a valve head 1218 (not shown)), and includes a first set of lateral relief cutouts 1504. The layer stack is disposed below a second side of the valve membrane 1220, and includes a load distribution layer 1316, a second elastomer layer 1506, and a plurality of support layers 1510. The load distribution layer 1316 is sandwiched between the valve membrane 1220 and the second elastomer layer 1506. In some implementations, the elastomer layer 1506 includes a second set of lateral relief cutouts 1508 corresponding to and aligning with the first set of lateral relief cutouts 1504. The load distribution layer 1316 partially extends from the edges of the second set of lateral relief cutouts 1508, and may flex into the second set of lateral relief cutouts 1508 in operation to increase the bend radius of the valve membrane 1220. In some arrangements, one or more of the cutouts of the second set of lateral relief cutouts 1508 may provide a portion of a path a fluid flow (e.g., may be in fluid communication with the outlet 1327). The elastomer layer 1506 further defines the valve seat 1322, and a portion of a fluid passage including a portion of the outlet 1327. In various arrangements, the top side of the first elastomer layer 1502 includes an anti-stiction coating to reduce wear caused by periodic engagement with a valve head (e.g., facing and corresponding to a footprint of a valve head). In addition, in various arrangements, the second side of the valve membrane 1220 may include an anti-stiction coating that faces and corresponds to the size of the valve seat 1322. Alternatively, the top surface of the valve seat 1322 includes an anti-stiction coating that faces the second side of the valve membrane 1220 and corresponds to the footprint of the valve seat 1322.

Figure 16:
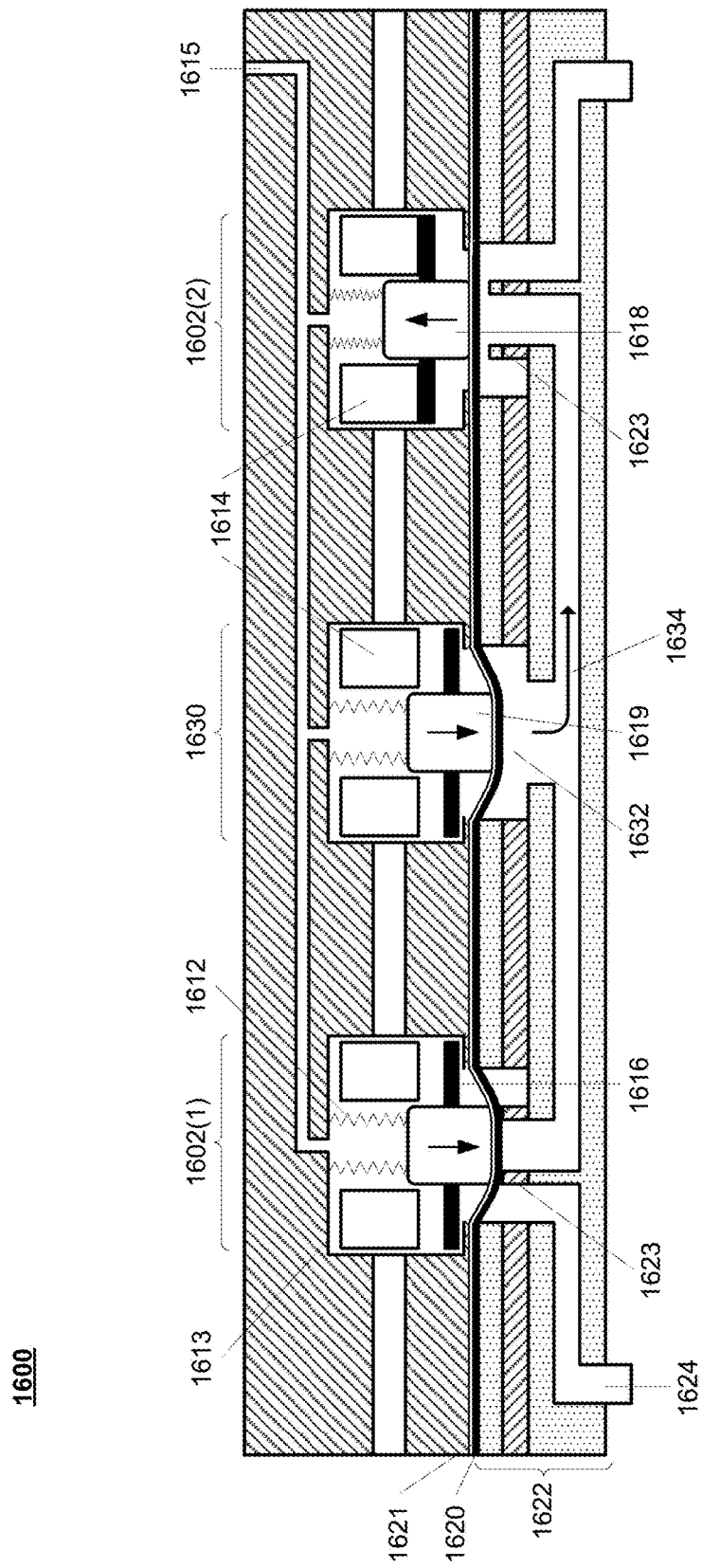
FIG. 16 is a cross-sectional illustration of a pump assembly.

FIG. 16 is a cross-sectional illustration of a pump assembly 1600, according to an example arrangement. In some implementations, the pump assembly 1600 is formed in a control plate, such as control plate 202 described above. The pump assembly 1600 includes a first valve assembly 1602(1) and a second valve assembly 1602(2) (each generally referred to as valve assembly 1602). The pump assembly 1600 also includes a fluid displacement assembly 1630.

Similar to the valve assembly 1200 described above in relation to FIG. 12A, each valve assembly 1602 includes a spring 1612, an electromagnet 1614, a washer 1616, a valve head 1618, a valve membrane 1620, and a layer stack 1622. Similar to the valve assembly 1310 discussed above in relation to FIG. 13A, the electromagnet 1614 is disposed within a vacuum chamber 1613. A vacuum external to the pump assembly 1600 applies a vacuum to the vacuum chamber 1613 via a vacuum line. Each valve assembly 1602 also includes a valve seat 1623 (which can, but need not, be formed from an elastomer) configured for operative engagement with the valve membrane 1620 to block the fluid flow through the layer stack 1622.

The fluid displacement assembly 1630 is configured in a similar fashion to the valve assembly 1602, except the fluid displacement assembly 1630 does not include a valve seat 1623. In addition, instead of a valve head 1618, the fluid displacement assembly 1630 includes a pump head 1619. When the pump head 1619 is driven down, the valve membrane 1620 is not driven into a valve seat 1623 to seal a portion of the of the fluid passage 1624 defined in the layer stack 1622. Rather, the movement of the pump head 1619 of the fluid displacement assembly 1630 generates a relative positive or negative pressure in the pump chamber 1632.

As described above, the electromagnet 1614 controls the state the valve head 1618. As illustrated in FIG. 16, no electrical input is provided to the electromagnet 1614 of the fluid displacement assembly 1630, and therefore there is little or no magnetic attraction between the electromagnet 1614 and its corresponding washer 1616. As such, the spring 1612 of the fluid displacement assembly 1630 presses the pump head 1619 into the valve membrane 1620, which creates a positive pressure in the pump chamber 1632. The positive pressure in the pump chamber 1632, in turn, forces fluid out of the pump chamber 1632 and generates a fluid flow 1634 through the layer stack 1622 toward the open, second valve assembly 1602(2), where an electrical input is provided to the corresponding electromagnet 1614. To prevent the backwards flow of fluid through the layer stack 1622, the first valve assembly 1602(1) is in the closed position.

To refill the pump chamber 1632, the process is reversed. The first valve assembly 1602(1) is opened and the second valve assembly 1602(2) is closed. An electrical input is provided to the electromagnet 1614 of the fluid displacement assembly 1630, which magnetically attracts and engages its washer 1616. The washer 1616 in turn compresses the spring 1612, drawing the valve head 1618 out of the pump chamber 1632. The upward deflection of the valve membrane 1620 generates a negative pressure in the pump chamber 1632, which draws fluid into the pump chamber 1632 via the open first valve assembly 1602(1).

As shown in FIG. 16, the pump assembly can also include an elastomer layer 1621 as part of the membrane or between the membrane and the valve heads 1618 and pump head 1620. In some implementations, at each of the valve heads 1618 and at the pump head 1620, the elastomer layer 1621 can have strain relief cutouts and/or an antistiction coating similar to what is shown in FIG. 14. In addition, or in the alternative, in some implementations of the pump assembly 1600, the valve membrane at each of the valve assemblies 1602 and/or at the fluid displacement assembly 1630 can include corrugations similar to those discussed in relation to FIG. 13B.

The invention may be embodied in other specific forms without departing from the spirit or essential characteristics thereof. The forgoing implementations are therefore to be considered in all respects illustrative, rather than limiting of the invention.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

Further, as utilized herein, the term "fluid" is intended to have a broad meaning in harmony with the common and accepted usage by those of ordinary skill in the art to which the subject matter of this disclosure pertains. In particular, it should be understood by those of skill in the art who review this disclosure that "fluid" contemplates matter capable exhibiting a flow, and may include matter in a gaseous state, a liquid state, or some combination of components in various states of matter.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is therefore to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The indefinite articles "a" and "an," as used herein in the specification and in the claims, unless clearly indicated to the contrary, should be understood to mean "at least one."

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. An apparatus comprising:
    a fluid flow plate comprising a plurality of polymer layers, the fluid flow plate defining a fluid flow passage through a microfluidic valve assembly; and
    the valve assembly, the valve assembly comprising:
        a valve seat;
        a valve head;
        a flexible membrane;
        an elastomer layer disposed on a first side of the flexible membrane between the flexible membrane and the valve head;
        a valve cavity positioned between the valve seat and a second side of the flexible membrane; and
        an actuator configured to selectively control pressure applied by the valve head to the elastomer layer, such that in a first actuator state the valve head depresses the flexible membrane into the valve cavity and moves the second side of the flexible membrane into contact with the valve seat, thereby preventing fluid flow through the valve assembly, and in a second state, the valve head and the flexible membrane are retracted substantially out of the valve cavity allowing fluid to flow through the valve assembly.

2. The apparatus of claim 1, wherein the flexible membrane is corrugated.

3. The apparatus of claim 2, wherein the valve seat is annular in shape, and the corrugations of the membrane are formed as concentric annular shapes that are coaxial to and outside the annulus of the valve seat.

4. The apparatus of claim 1, wherein the fluid flow plate comprises a flexible load distribution layer coupled to a valve seat facing side of the flexible membrane, the load distribution layer having a cutout above the valve seat, wherein the diameter of the cutout in the load distribution layer is larger than an outer diameter of the valve seat and less than a diameter of the valve cavity.

5. The apparatus of claim 1, comprising an anti-stiction coating disposed on at least one of a valve head facing surface of the flexible membrane over an area corresponding to a valve head footprint, a valve seat facing surface of the flexible membrane over an area corresponding to a valve seat footprint, and a membrane facing surface of the valve seat.

6. The apparatus of claim 1, further comprising a vacuum chamber defined by an airtight housing and a valve head facing surface of the flexible membrane.

7. The apparatus of claim 1, wherein the flexible membrane has a tensile strain in the second state of between about 0.25% and about 2.0%.

8. The apparatus of claim 1, wherein the valve seat has a resting tensile strain in the second state of between about 0.25% and about 2.0%.

9. The apparatus of claim 1, wherein the flexible membrane further comprises layer of a biocompatible metal.

10. The apparatus of claim 1, wherein the elastomer layer includes a plurality of lateral strain relief cutouts disposed in a common plane and distributed radially about an area corresponding to a valve seat footprint of the elastomer layer.

11. The apparatus of claim 1, wherein the valve seat comprises an elastomer layer.

12. An apparatus comprising:
    a fluid flow plate comprising a plurality of polymer layers, the fluid flow plate defining a fluid flow passage through a microfluidic valve assembly; and
    the valve assembly, the valve assembly comprising:
        a valve seat comprising an elastomer layer;
        a flexible membrane;

a valve cavity positioned between the valve seat and the flexible membrane;

a valve head; and an actuator configured to selectively control pressure applied by the valve head to the flexible membrane, such that in a first actuator state the valve head depresses the flexible membrane into the valve cavity and into contact with the valve seat, thereby preventing fluid flow through the valve assembly, and in a second state, the valve head and the flexible membrane are retracted substantially out of the valve cavity allowing fluid to flow through the valve assembly.

13. The apparatus of claim 12, wherein the flexible membrane is corrugated.

14. The apparatus of claim 13, wherein the valve seat is annular in shape, and the corrugations of the membrane are formed as concentric annular shapes that are coaxial to and outside the annulus of the valve seat.

15. The apparatus of claim 12, wherein the fluid flow plate comprises a flexible load distribution layer coupled to a valve seat facing side of the flexible membrane, the load distribution layer having a cutout above the valve seat, wherein the diameter of the cutout in the load distribution layer is larger than an outer diameter of the valve seat and less than a diameter of the valve cavity.

16. The apparatus of claim 12, comprising an anti-stiction coating disposed on at least one of a valve head facing surface of the flexible membrane over an area corresponding to a valve head footprint, a valve seat facing surface of the flexible membrane over an area corresponding to a valve seat footprint, and a membrane facing surface of the valve seat.

17. The apparatus of claim 12, further comprising a vacuum chamber defined by an airtight housing and a valve head facing surface of the flexible membrane.

18. The apparatus of claim 12, wherein the flexible membrane has a tensile strain in the second state of between about 0.25% and about 2.0%.

19. The apparatus of claim 12, wherein the valve seat has a resting tensile strain in the second state of between about 0.25% and about 2.0%.

20. The apparatus of claim 12, wherein the flexible membrane is formed of at least one of an elastomer and a biocompatible metal.

21. The apparatus of claim 12, wherein the membrane comprises a second elastomer layer and the second elastomer layer includes a plurality of lateral strain relief cutouts disposed radially about an area corresponding to a valve seat footprint of the elastomer layer.

* * * * *